(12) United States Patent
Decker et al.

(10) Patent No.: US 10,468,904 B2
(45) Date of Patent: *Nov. 5, 2019

(54) SYSTEM FOR WIRELESS CHARGING OF A BATTERY WITHIN A STERILIZABLE VESSEL

(71) Applicant: Greatbatch Ltd., Clarence, NY (US)

(72) Inventors: Gregory G. Decker, Taunton, MA (US); Brian R. Peterson, Cumberland, RI (US); Eric Jankins, Raynham, MA (US); William A. Planck, Hillsboro, OR (US); Leslie I. Halberg, Valencia, CA (US); Jason Hamilton, Dartmouth, MA (US)

(73) Assignee: Greatbatch Ltd., Clarence, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/386,333

(22) Filed: Apr. 17, 2019

(65) Prior Publication Data

US 2019/0245374 A1 Aug. 8, 2019

Related U.S. Application Data

(63) Continuation of application No. 16/194,458, filed on Nov. 19, 2018, now Pat. No. 10,312,722, which is a continuation of application No. 15/339,960, filed on Nov. 1, 2016, now Pat. No. 10,236,709.

(60) Provisional application No. 62/332,159, filed on May 5, 2016.

(51) Int. Cl.
*H01M 10/46* (2006.01)
*H02J 7/02* (2016.01)
*H02J 50/00* (2016.01)
*H02J 50/12* (2016.01)
*A61L 2/26* (2006.01)
*A61L 2/07* (2006.01)
*H02J 50/50* (2016.01)

(52) U.S. Cl.
CPC ............... *H02J 7/025* (2013.01); *A61L 2/26* (2013.01); *H02J 50/00* (2016.02); *H02J 50/12* (2016.02); *A61L 2/07* (2013.01); *H02J 50/50* (2016.02)

(58) Field of Classification Search
CPC .......... H02J 7/355; H02J 7/0042; H02J 5/005; H02J 7/025; H02J 50/10; H02J 50/90
USPC .................. 320/107, 108, 114, 115; 307/104
See application file for complete search history.

(56) References Cited

U.S. PATENT DOCUMENTS

| | | | |
|---|---|---|---|
| 6,067,474 A | 5/2000 | Schulman et al. | |
| 6,847,190 B2 | 1/2005 | Schaefer et al. | |
| 7,362,228 B2 | 4/2008 | Tethrake et al. | |
| 7,638,958 B2 | 12/2009 | Philipp et al. | |

(Continued)

OTHER PUBLICATIONS

Extended European Search Report, Application No. 16197147.8 dated Sep. 14, 2017.

*Primary Examiner* — Edward Tso
(74) *Attorney, Agent, or Firm* — Michael P. Horvath

(57) ABSTRACT

In various examples, a system includes a power generating device configured to generate and transfer power to an electrical device. A sterilizable vessel is configured to accommodate the electrical device. The vessel is configured to allow power to be at least partially wirelessly transferred from the power generating device, through the vessel, and to the electrical device. In other examples, a method includes wirelessly powering and/or charging an electrical device disposed within a sterilizable vessel.

20 Claims, 20 Drawing Sheets

(56) References Cited

U.S. PATENT DOCUMENTS

| | | |
|---|---|---|
| 8,035,255 B2 | 10/2011 | Hall et al. |
| 8,061,014 B2 | 11/2011 | Bales et al. |
| 9,240,630 B2 | 1/2016 | Himanshu |
| 10,312,722 B2 * | 6/2019 | Decker .................. H02J 50/12 |
| 2007/0048176 A1 | 3/2007 | Orrico et al. |
| 2010/0156723 A1 | 6/2010 | Luch |
| 2010/0161002 A1 | 6/2010 | Aghassian et al. |
| 2012/0062171 A1 | 3/2012 | Smith et al. |
| 2012/0218068 A1 | 8/2012 | Yamakawa et al. |
| 2012/0223595 A1 | 9/2012 | Oodachi et al. |
| 2014/0091636 A1 | 4/2014 | Ofstein et al. |
| 2014/0266921 A1 | 9/2014 | Joshi et al. |
| 2015/0130409 A1 | 5/2015 | Lee et al. |
| 2015/0171658 A1 | 6/2015 | Manova-Elssibony et al. |
| 2015/0182230 A1 | 7/2015 | Krishnamurthy et al. |
| 2015/0207337 A1 | 7/2015 | Peterson et al. |
| 2015/0280450 A1 | 10/2015 | Park et al. |

\* cited by examiner

SYSTEM FOR WIRELESS CHARGING OF A BATTERY WITHIN A STERILIZABLE VESSEL

CROSS REFERENCE TO RELATED APPLICATIONS

This application is a continuation of and claims the benefit of priority under 35 U.S.C. § 120 to Decker et al., U.S. patent application Ser. No. 16/194,458, now U.S. Pat. No. 10,312,722, filed on Nov. 19, 2018, entitled "SYSTEM FOR WIRELESS CHARGING OF A BATTERY WITHIN A STERILIZABLE VESSEL," which is a continuation of and claims the benefit of priority under 35 U.S.C. § 120 to Decker et al., U.S. patent application Ser. No. 15/339,960, now U.S. Pat. No. 10,236,709, filed on Nov. 1, 2016, entitled "APPARATUS, SYSTEM, AND METHOD FOR WIRELESS CHARGING OF A DEVICE WITHIN A STERILIZABLE VESSEL," which claims the benefit of priority to U.S. Provisional Application Ser. No. 62/332,159, filed on May 5, 2016, entitled "WIRELESSLY CHARGING IN A STERILIZABLE ENCLOSURE," each of which is incorporated by reference herein in its entirety.

BACKGROUND

The present invention relates to charging of a device within a sterilizable vessel, and more specifically relates to wirelessly charging of a device within a sterilizable vessel without compromising the sterile field of the vessel.

Powering and/or charging of electrical devices within a sterilized vessel can be problematic. Such vessels used to sterilize devices (for instance, using an autoclaving or other sterilization process) include trays and sterilizable containers. A tray, along with its contents to be sterilized, is typically wrapped in an antimicrobial cloth or barrier, which allows the tray and its contents to be autoclaved or otherwise sterilized. A sterilizable container and its contents can be sterilized without being wrapped in an antimicrobial cloth or barrier, as the contents are sealable within the sterilizable container and able to be sterilized within the container. Powering and/or charging of a sterilized electrical device within a tray or sterilizable container is a challenge because, typically, the electrical device cannot simply be plugged in to a power source without breaking the sterile field.

Therefore, generally speaking, electrical devices, such as, for instance, batteries, to be sterilized are typically charged prior to sterilization. However, charging of batteries prior to sterilization has various disadvantages. For instance, subsequent autoclaving of a fully-charged battery can result in damage to and/or decreased longevity of the battery due to forces within the battery resulting from the raising of the temperature of a fully-charged battery. Additionally, because the charge of a battery decreases over time, what goes on the storage shelf as a fully-charged, sterilized battery can come off the shelf with significantly less charge, depending upon the amount of time the battery was in storage, potentially resulting in the need to pull another sterilized battery off the shelf in order to complete a procedure. In order to recharge or determine the status of a previously-charged, sterilized battery, the battery would typically have to be removed from the sterilized tray or container, checked and/or charged, and then placed back into a tray or sterilizable container and sterilized again.

Overview

This overview is intended to provide an overview of subject matter of the present patent document. It is not intended to provide an exclusive or exhaustive explanation of the invention. The detailed description is included to provide further information about the present patent document.

The present inventors have recognized, among other things, that the subject matter can be used with respect to charging of a device within a sterilizable vessel. In various examples, the apparatus, system, and method can include at least an aspect of wirelessly powering and/or charging for the device within the sterilizable vessel. The present inventors have recognized the present subject matter can be used to maintain ease-of-use, allow for post-autoclave charging of batteries, and retain vessel durability. To better illustrate the apparatuses, systems, and methods described herein, a non-limiting list of examples is provided here:

Example 1 can include subject matter that can include a system including a power generating device configured to generate and transfer power to an electrical device. A sterilizable vessel is configured to accommodate the electrical device. The vessel is configured to allow power to be at least partially wirelessly transferred from the power generating device, through the vessel, and to the electrical device.

In Example 2, the subject matter of Example 1 is optionally configured such that the power generating device includes a source coil and the electrical device includes a receiving coil. The source coil is configured to transmit electromagnetic waves to the receiving coil to wirelessly transfer power from the power generating device to the electrical device.

In Example 3, the subject matter of Example 2 is optionally configured such that the vessel includes a repeater coil configured to receive the electromagnetic waves and transmit the electromagnetic waves to the receiving coil to wirelessly transfer power from the power generating device, through the vessel, and to the electrical device.

In Example 4, the subject matter of any one of Examples 1-3 is optionally configured such that the power generating device includes a source coil and the vessel includes a receiving coil. The electrical device is electrically coupled to the receiving coil of the vessel. The source coil is configured to transmit electromagnetic waves to the receiving coil to at least partially wirelessly transfer power from the power generating device to the electrical device.

In Example 5, the subject matter of any one of Examples 1-4 is optionally configured such that the vessel includes a source coil and the electrical device includes a receiving coil. The power generating device is electrically coupled to the source coil of the vessel. The source coil is configured to transmit electromagnetic waves to the receiving coil to at least partially wirelessly transfer power from the power generating device to the electrical device.

In Example 6, the subject matter of any one of Examples 1-5 is optionally configured such that the vessel includes a tray sized and shaped to accommodate at least one electrical device within an interior of the tray.

In Example 7, the subject matter of any one of Examples 1-6 is optionally configured such that the vessel includes a sterilizable container sized and shaped to accommodate at least one electrical device within an interior of the sterilizable container.

In Example 8, the subject matter of Example 7 is optionally configured such that the sterilizable container includes a closure, which, when in a closed position, seals the interior of the sterilzable container.

In Example 9, the subject matter of any one of Examples 1-8 is optionally configured such that the electrical device includes a battery configured to be wirelessly charged by the power generating device.

In Example 10, the subject matter of any one of Examples 1-9 is optionally configured such that the vessel includes an opening in a wall of the vessel. The opening is configured to allow wireless power transfer through the wall of the vessel from the power generating device to the electrical device.

In Example 11, the subject matter of Example 10 is optionally configured such that a non-metallic material is disposed within the opening.

In Example 12, the subject matter of any one of Examples 1-11 is optionally configured such that a wall of the vessel includes a metallic material. A thickness of the wall is configured to allow wireless power transfer through the wall of the vessel from the power generating device to the electrical device.

In Example 13, the subject matter of any one of Examples 1-12 is optionally configured such that a wall of the vessel includes a metallic material. The power generating device is configured to transmit power at a frequency that allows wireless power transfer through the wall of the vessel from the power generating device to the electrical device.

In Example 14, the subject matter of any one of Examples 1-13 is optionally configured such that a wall of the vessel includes a non-metallic material to allow wireless power transfer through the wall of the vessel from the power generating device to the electrical device.

Example 15 can include, or can optionally be combined with any one of Examples 1-14 to include subject matter that can include a system for wirelessly recharging a battery. The system includes a power generating device configured to generate and transfer power to the battery. A sterilizable vessel is sized and shaped to accommodate the battery within an interior of the vessel. The vessel is configured to allow power to be at least partially wirelessly transferred from the power generating device, through the vessel, and to the battery to charge the battery.

In Example 16, the subject matter of Example 15 is optionally configured such that the power generating device includes a source coil and the battery includes a receiving coil. The source coil is configured to transmit electromagnetic waves to the receiving coil to wirelessly transfer power from the power generating device to the battery to charge the battery within the vessel.

In Example 17, the subject matter of Example 16 is optionally configured such that the vessel includes a repeater coil configured to receive the electromagnetic waves and transmit the electromagnetic waves to the receiving coil to wirelessly transfer power from the power generating device, through the vessel, and to the battery.

In Example 18, the subject matter of any one of Examples 15-17 is optionally configured such that the power generating device includes a source coil and the vessel includes a receiving coil. The battery is electrically coupled to the receiving coil of the vessel. The source coil is configured to transmit electromagnetic waves to the receiving coil to at least partially wirelessly transfer power from the power generating device to the battery to charge the battery within the vessel.

In Example 19, the subject matter of any one of Examples 15-18 is optionally configured such that the vessel includes a source coil and the battery includes a receiving coil. The power generating device is electrically coupled to the source coil of the vessel. The source coil is configured to transmit electromagnetic waves to the receiving coil to at least partially wirelessly transfer power from the power generating device to the battery to charge the battery within the vessel.

In Example 20, the subject matter of any one of Examples 15-19 is optionally configured such that the vessel includes an opening in a wall of the vessel. The opening is configured to allow wireless power transfer through the wall of the vessel from the power generating device to the battery.

DETAILED DESCRIPTION

Figure 1:
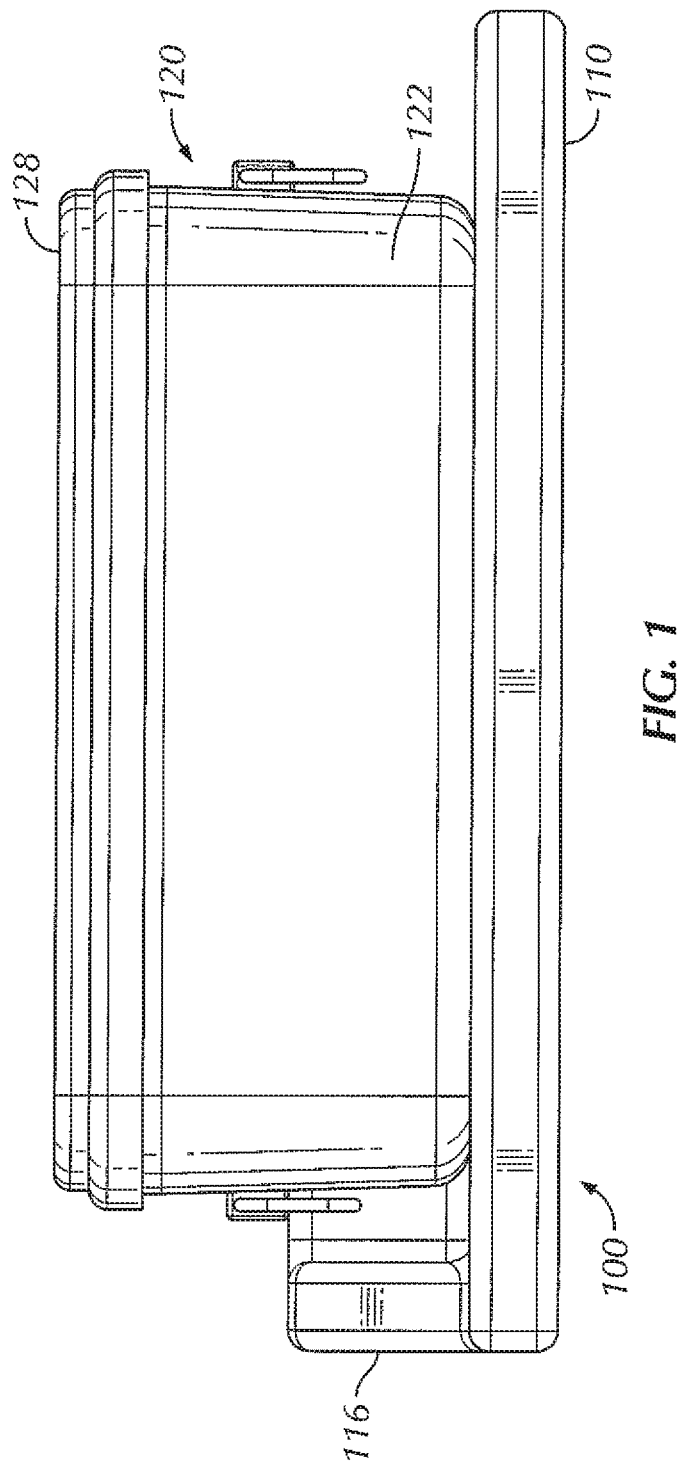
FIG. 1 is a side view of a system in accordance with at least one example of the invention.
Figure 2:
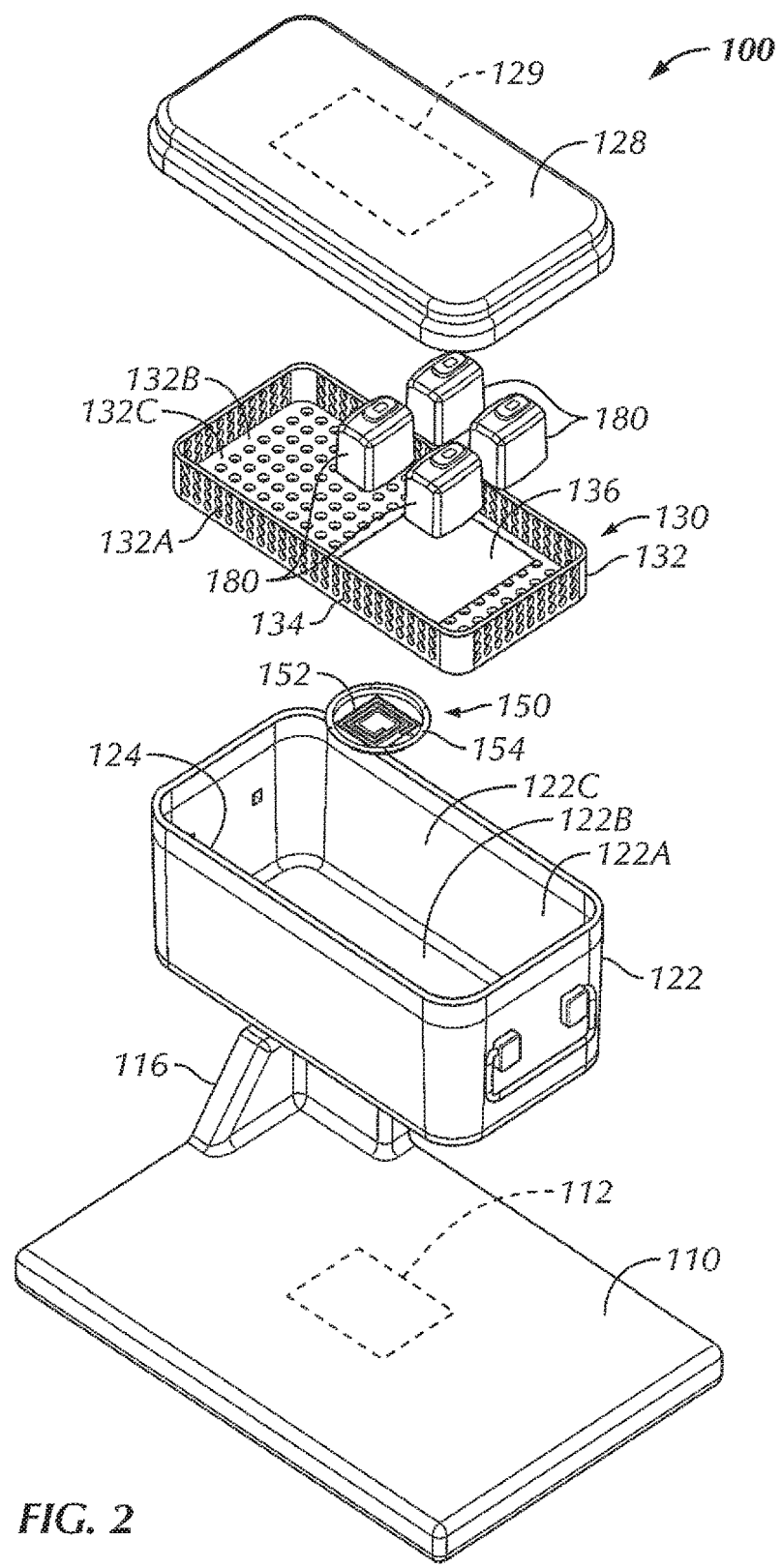
FIG. 2 is an exploded view of the system of FIG. 1.
Figure 3:
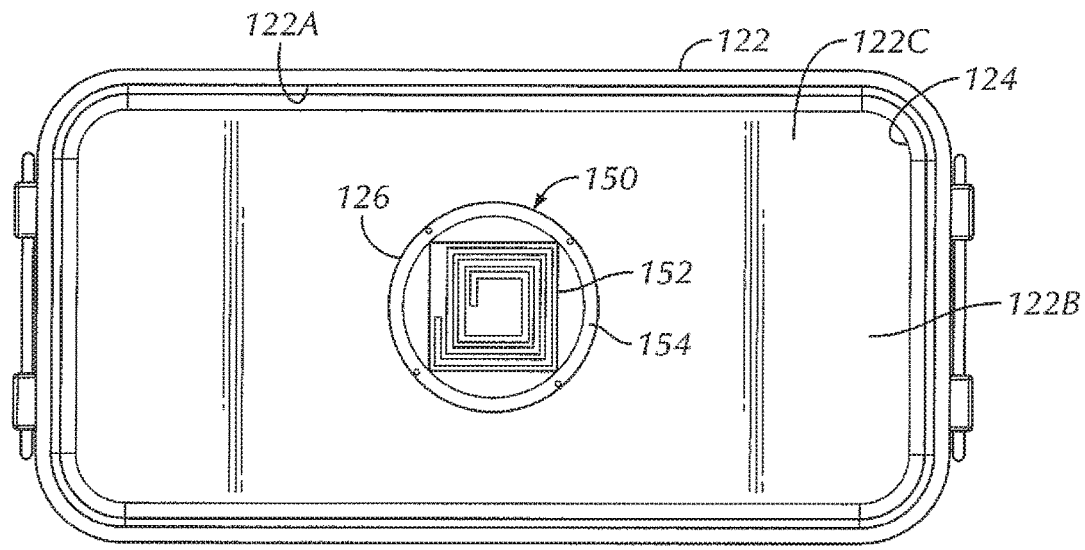
FIG. 3 is a top view of an interior of a sterilizable container of the system of FIG. 1.

The present patent application relates to an apparatus, system, and method for charging of a device within a sterilizable vessel. In various examples, as described herein, the apparatus, system, and method can include at least an aspect of wirelessly powering and/or charging for the device within the sterilizable vessel. In some examples, the device can include an electrical device, such as, but not limited to a battery, an electrical surgical tool (such as a drill, a saw, a cauterizer, etc.), a physiological parameter measuring or monitoring device, a device for administering treatment (such as a fluid pump, an electrical stimulation device, etc.), or the like. In further examples, the device can include a battery for an electrical device, such as, but not limited to, the above examples of electrical devices.

Wireless power in general and magnetic resonance in particular is capable of delivering power to devices through many materials. Metals, however, can provide an obstacle to wireless power because the energy is absorbed by the material in accordance with the skin effect, or the depth to which an electric current penetrates the surface of the metal conductor. The depth to which the current will flow in a metal is inversely proportional to the frequency of the signal being transmitted.

When a magnetic field is introduced to a metal surface, current is induced in the metal. If the frequency of the introduced signal is such that the skin depth is larger than the thickness of the metal surface, the induced current will flow through the entire material and will create an opposing field that will block the original field from penetrating the material. This phenomenon is called a shield current, and it is a reason why metal enclosures are used to shield devices from Electro Magnetic radiation.

A problem arises when an enclosure is desirable for an application but the shielding properties of that enclosure are not. For example, if a device within the enclosure has a requirement to be powered wirelessly, such as through highly resonant wireless power delivery, the metal enclosure can hinder that goal. The example systems, apparatuses, and methods described herein seek to decrease the hindrance that enclosures, such as metal enclosures, can cause with respect to wirelessly powering a device.

In some examples, the present systems, apparatuses, and methods seek to wirelessly charge a surgical battery pack within a sterilizable vessel (a sterilizable container, a tray, or the like) in which the packs are autoclaved. An autoclave is a cleaning device that heats an object or device to a high temperature to sterilize it. In some examples, the present systems, apparatuses, and methods seek to wirelessly charge a surgical battery pack within a sealed serializable bag, either in addition to or instead of charging the surgical battery pack within a sterilizable vessel.

Charging the battery prior to autoclave poses challenges to the battery itself. Having batteries that can survive and go through autoclave sterilization is a current industry challenge. An issue is that the cell chemistry does not like to be heated up as it changes/causes chemical reactions and break downs to occur within the cell. Heating a battery that is charged can cause pressure to build up in the cells that can lead to cell damage or capacity loss in the battery. It is, therefore, desirable to charge the battery after autoclave has already been completed. However, charging the battery after autoclave by conventional, contacted means will necessarily break the sterile field, meaning that the charged battery would have to be sterilized again, which resurrects the challenges heretofore mentioned. Being able to charge the batteries after autoclave can facilitate the batteries having a longer usable life (cycle count) while also allowing for little to no charge to be lost during autoclave. Additionally, there is the potential to reduce the process steps in that the batteries can be charged after autoclave. In this way, by wirelessly charging batteries, the batteries can be treated like other unpowered instrument in that there would be no need to plug the batteries in and wait for them to charge before they are sterilized.

In some examples, wireless charging of a battery allows the battery to be charged after autoclave without breaking the sterile field. A challenge to wireless charging after autoclave is the vessel (such as a sterilizable container, a tray, or the like) in which the battery is autoclaved.

Typically the objects placed into the autoclave are placed in a metal tray because the metal is easily cleaned and is typically fairly durable through multiple high temperature cycles through the autoclave. In various examples of the systems, apparatuses, and methods described herein, a wirelessly charged battery can be charged without special handling of the battery before and/or after autoclave, which would break the sterile seal.

Figure 7:
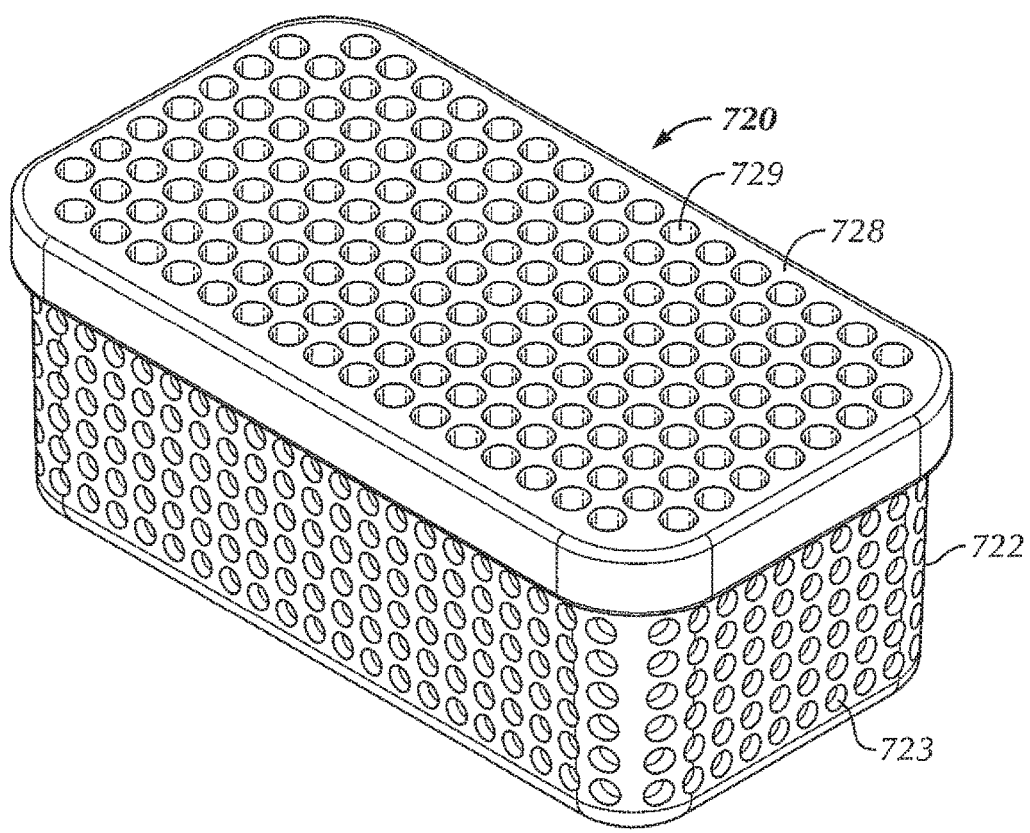
FIG. 7 is a perspective view of a tray for use with a system in accordance with at least one example of the invention.
Figure 8:
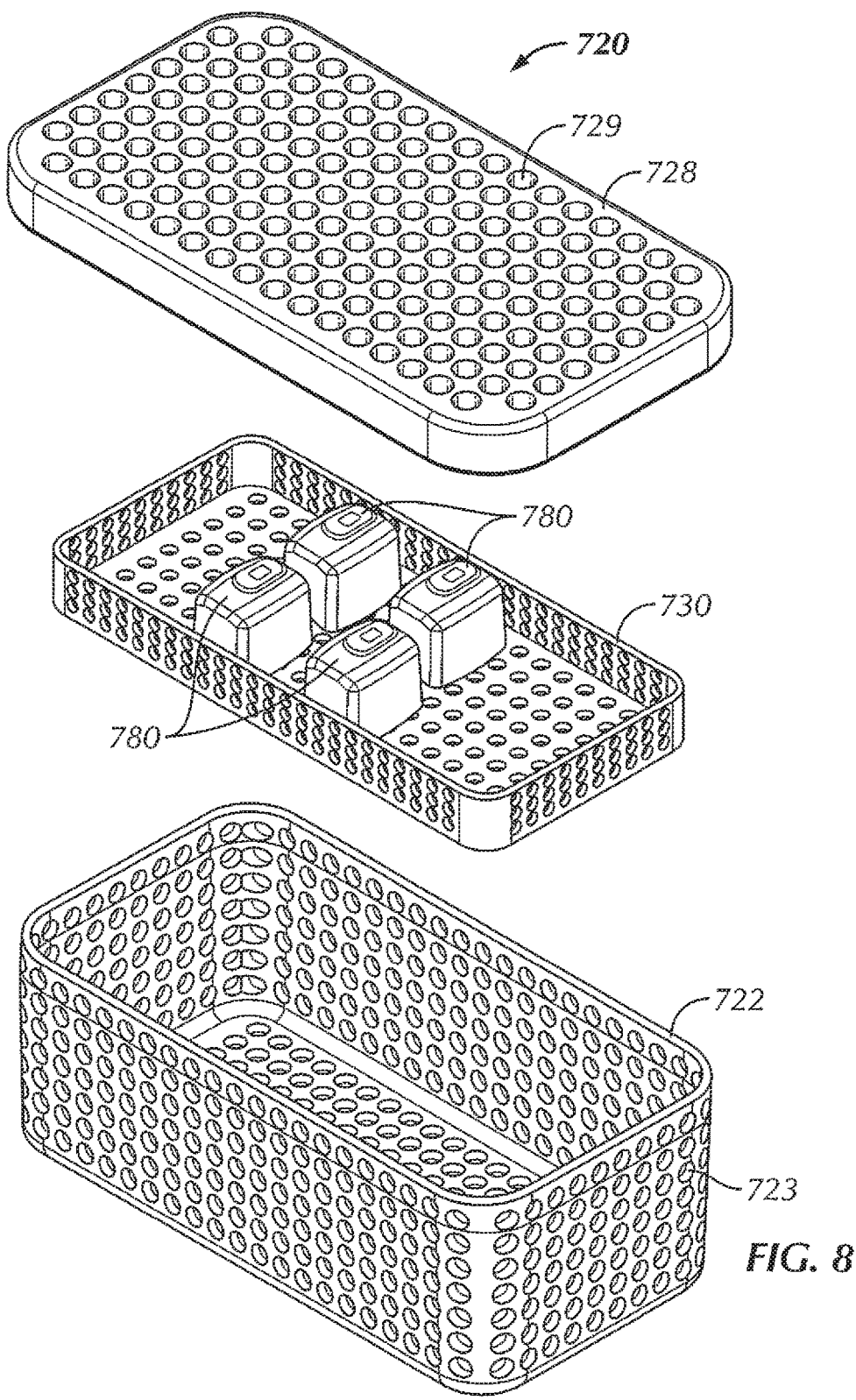
FIG. 8 is a perspective view of the tray of FIG. 7.
Figure 9:
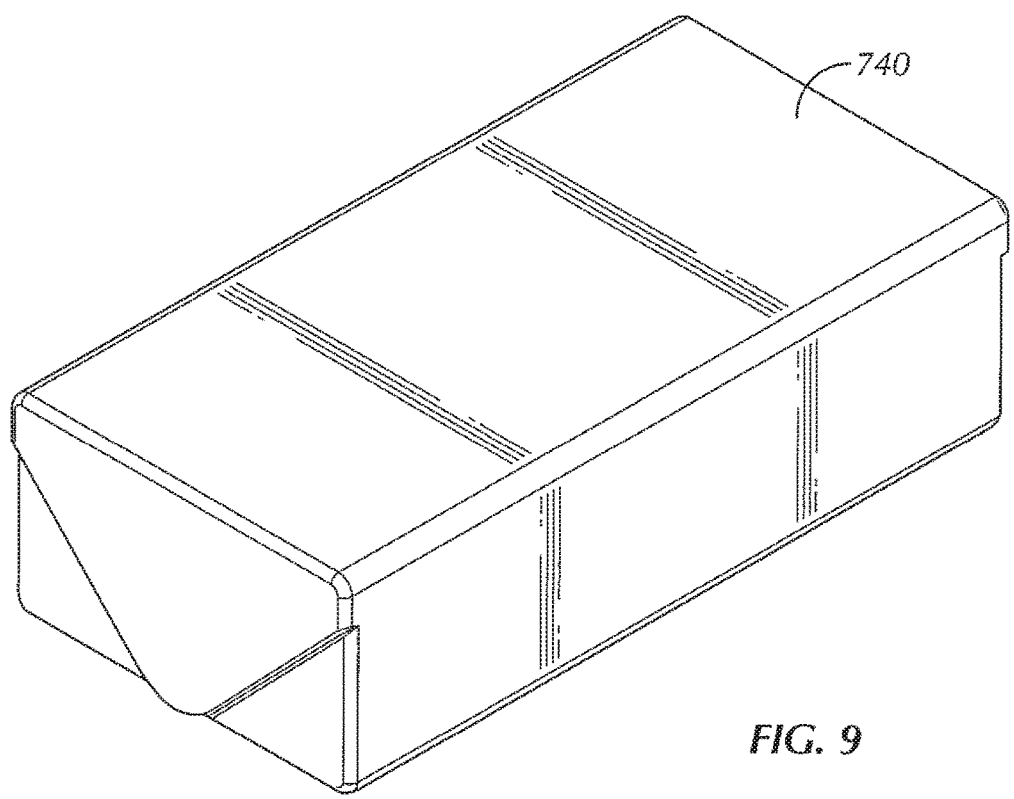
FIG. 9 is a perspective view of the tray of FIG. 7 wrapped in an antimicrobial material.
Figure 10:
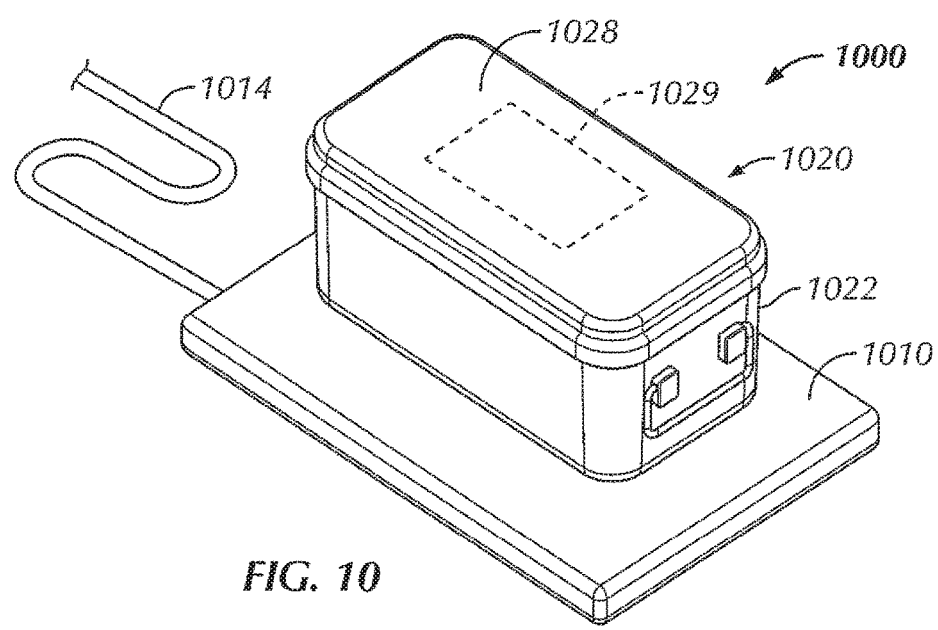
FIG. 10 is a perspective view of a system in accordance with at least one example of the invention.
Figure 11:
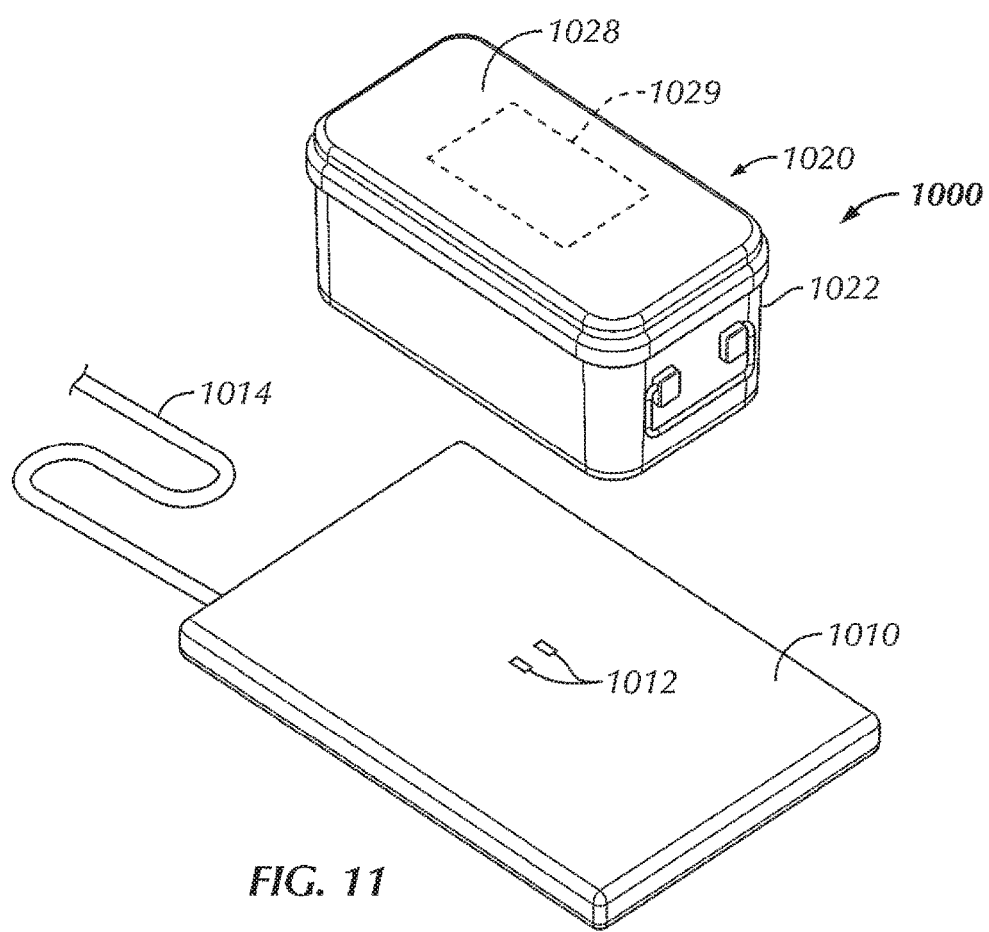
FIG. 11 is a perspective view of the system of FIG. 10 with a sterilizable container lifted off of a base unit.
Figure 12:
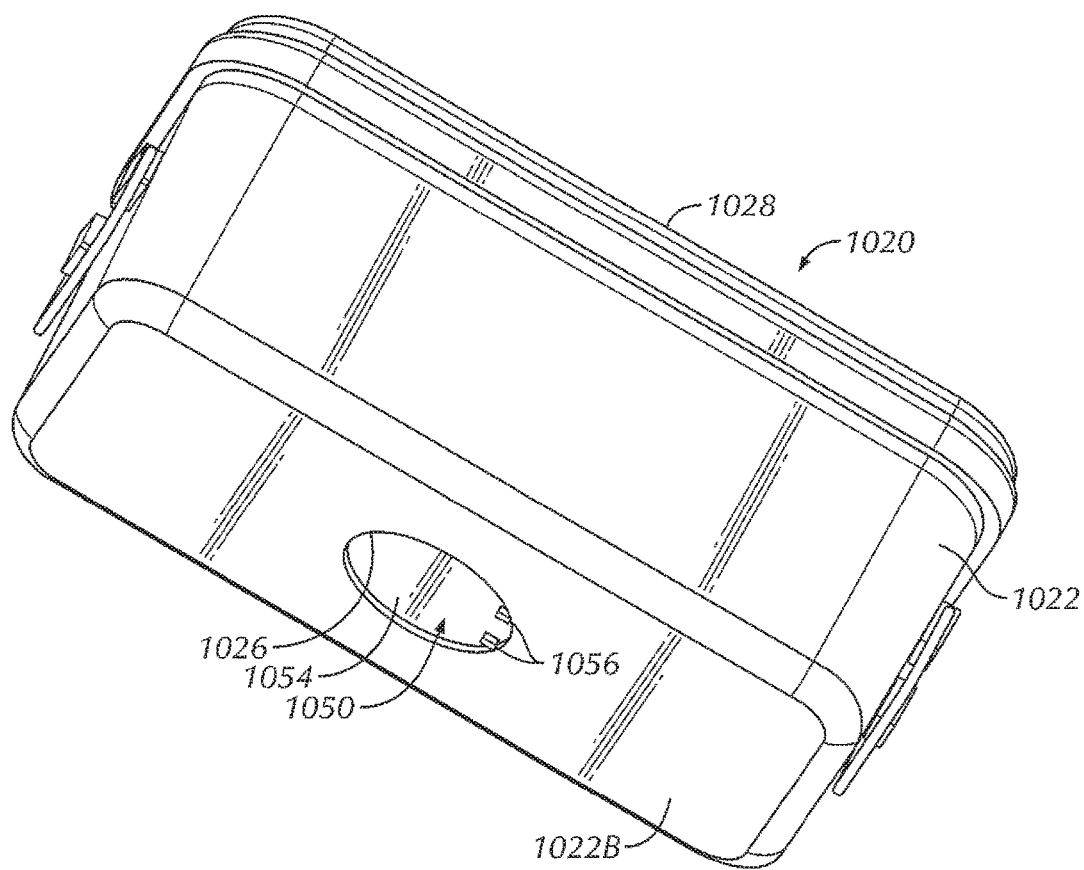
FIG. 12 is a perspective view of a bottom of a sterilizable container of the system of FIG. 10.
Figure 13:
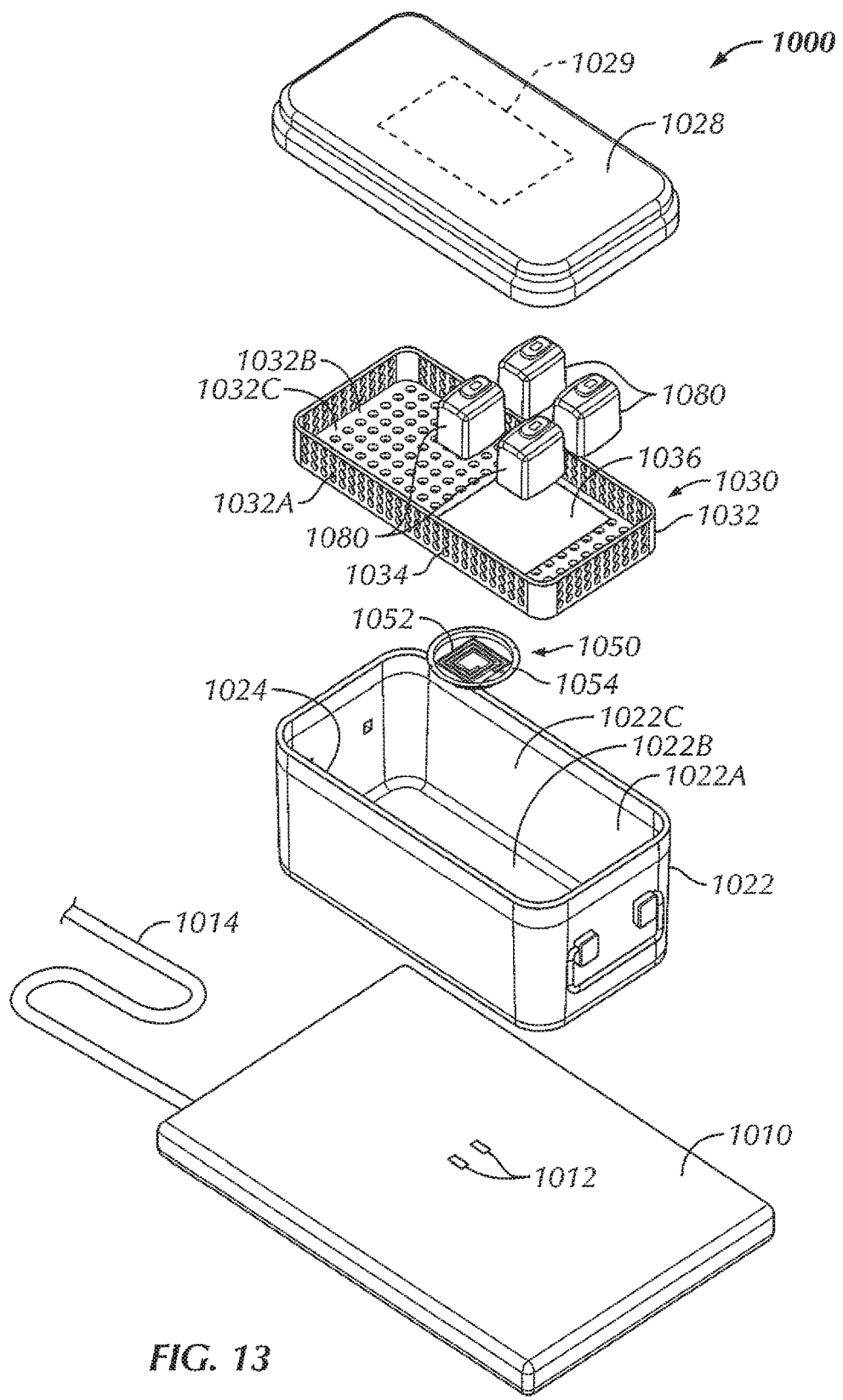
FIG. 13 is an exploded view of the system of FIG. 10.

Referring briefly to FIGS. 7-9, a tray 720 typically includes a bottom portion 722 and a lid 728, both of which typically include apertures or openings 723, 729 to allow steam and heat of an autoclave to penetrate an interior of the tray 720 to sterilize contents 780 of the tray 720. Component trays 730 are often placed inside the tray 720. An antimicrobial material or wrap 740 is typically used to wrap the tray 720 prior to sterilization, wherein the antimicrobial material 740 allows the contents 780 of the tray 720 to be sterilized during autoclaving and maintains the sterile barrier after sterilization.

A sterilizable container is typically a solid metal box with a closure or lid that, when closed, creates a hermetic seal with the box. A filter is typically disposed on the top of the sterilizable container to allow for heat and steam to penetrate the sterilizable container during the autoclave cycle and maintain the sterile barrier after sterilization of the contents of the sterilizable container. Component trays or holders are often placed inside the sterilizable containers. Sterilizable containers do not require an antimicrobial material or wrap because the sterilizable container itself forms a hermetic seal around the contents with the lid sealed. Therefore, the exterior of the sterilizable container can be stored, handled, etc. post sterilization and the contents of the sterilizable container remain sterilized.

In typical applications, the sterilizable vessel is formed from metal, such as stainless steel or aluminum, to maximize durability during handling and multiple thermal cycles. The systems, apparatuses, and methods described in various examples herein seek to maintain ease-of-use, allow for post-autoclave charging of batteries, and retain vessel durability.

Additionally, communications such as state of health (SOH) and state of charge (SOC) is currently only known prior to autoclave as again coming into contact with the battery directly is not possible without breaking the sterile barrier. Being able to determine a status of a battery prior to being brought into the operating room would be advantageous as it can save time and lessen, if not eliminate, the need to have one or more spare batteries brought into the operating room. The systems, apparatuses, and methods described in various examples herein seek to allow for communication to the battery without breaking the sterile barrier in order to determine various information about the battery, such as, but not limited to, SOH and SOC.

Charging a battery post autoclave can increase the likelihood that the batteries are fully charged prior to going into the operating room. Having a communication link can allow for the SOH and SOC to be known, for instance, moments before the sterile barrier is broken. One or both of these features of the systems, apparatuses, and methods described in various examples herein can allow for a more reliable product and lessen, if not eliminate, the risk of getting a bad battery that may have been damaged in the autoclaving process.

Referring now to FIGS. 1-6, in some examples, a system 100 is configured to wirelessly power an electrical device 180 within a sterilizable vessel 120. In some examples, an interior of the sterilizable vessel 120 is sized and shaped to accommodate at least one electrical device 180 within the interior of the sterilizable vessel 120. In some examples, as will be described in more detail herein, a power generating device 110 is configured to generate and transfer power to the electrical device 180. In some examples, the sterilizable vessel 120 is configured to accommodate the electrical device 180, the sterilizable vessel 120 being configured to allow power to be at least partially wirelessly transferred from the power generating device 110, through the sterilizable vessel 120, and to the electrical device 180. As used herein, the phrase "at least partially wirelessly transferred" is intended to mean that at least a portion of the power transfer from one point or device to another point or device is done wirelessly, even though some aspects of the power transfer can be direct or wired.

In the example shown in FIGS. 1-6, the sterilizable vessel 120 includes a sterilizable container 120. In various examples, the sterilizable container 120 can be formed from a metallic material. For instance, in some examples, the sterilizable container 120 can be formed from stainless steel. In other examples, the sterilizable container 120 can be formed from aluminum. In some examples, the sterilizable container 120 includes a box 122 including sidewalls 122A and a bottom 122B, the box 122 including an opening 124 to access an interior 122C of the box 122. In some examples, the opening 124 is in a top of the box 122. The sterilizable container 120, in some examples, includes a closure or lid 128 that, when in a closed position (FIGS. 1 and 5), seals the opening 124 and the interior 122C of the box 122. A portion of the sterilizable container 120, in some examples, includes an antimicrobial filter 129 configured to allow heat and steam within the sterilizable container 120 with the lid 128 closed (for instance, during an autoclave process) but not allow contaminants into the sterilizable container 120 in order to maintain a sterile environment within the sterilizable container 120. In some examples, the antimicrobial filter 129 is disposed within the lid 128. In other examples, an antimicrobial filter can be disposed within one or more of the sidewalls 122A of the box 122 and/or the bottom 122B of the box 122.

Within the interior 122C of the sterilizable container 120, in some examples, is a component tray 130 configured to hold one or more components, such as one or more electrical devices 180, within the sterilizable container 120 for sterilization. In some examples, the component tray 130 is removable from within the interior 122C of the sterilizable container 120. In some examples, the component tray 130 includes a tray portion 132 having sidewalls 132A and a bottom 132B, the tray portion 132 defining an interior 132C configured to hold one or more components therein, for instance, during an autoclave process or other sterilization procedure. In some examples, at least a portion of the tray portion 132 includes holes or openings 134 therethrough to allow steam and/or heat from the autoclave process or other sterilization procedure to penetrate the interior 132C of the tray portion 132 and envelop the one or more components in order to sterilize the one or more components. In some examples, the component tray 130 is sized and shaped to freely slide into and out of the interior 122B of the box 122, for example, when a user is inserting the component tray 130 into the box 122 and taking the component tray 130 out of the box 122, for instance, to insert or remove one or more components (such as one or more electrical devices 180). In some examples, the bottom 132B of the component tray 130 is configured to rest at least a distance from the bottom 122B of the box. In this way, in some examples, the distance allows for the one or more components to rest spaced from the bottom 122B of the box 122 in the event that excess heat builds up at the bottom 122B of the box 122 or condensation and/or water pools at the bottom 122B of the box 122, so as to decrease the chances that the one or more components become damaged by excessive heat and/or by becoming at least partially submerged in pooling water.

In some examples, the system 100 includes the power generating device 110. In some examples, the power generating device 110 is a base 110 that is sized and shaped to allow a sterilizable container 120 to be placed on top of the base 110. The base 110, in some examples, is connectable to power, such as, but not limited to, by plugging a power cord of the base 110 into a wall outlet. The base 110 includes, in various examples, a source coil 112 positioned within the base 110 so as to be in proximity to the sterilizable container 120 with the sterilizable container 120 being situated on or otherwise in place with respect to the base 110. In some examples, the source coil 112 of the base 110 is configured to generate an electromagnetic field for wirelessly transferring power to the one or more electric devices 180.

However, due to the enclosed nature of a typical sterilizable container, the passing of the electromagnetic field and, in turn, the transferring of power, through a typical sterilizable container is at least hindered, if not completely obstructed. The sterilizable container 120, in some examples, includes an aperture or opening 126 in the box 122. In some examples, the opening 126 is disposed within the bottom 122B of the box 122, although in other examples, the opening can be disposed within other portions of the box 122, depending upon the positioning of the source coil 112 within the base 110. In some examples, the opening 126 of the sterilizable container 120 is positioned to be aligned with the source coil 112 of the base 110 with the sterilizable container 120 in position for power transfer on the base 110. In some examples, the base 110 can include an alignment feature 116 configured to assist in aligning the source coil 112 with the opening 126 of the sterilizable container 120. In some examples, the alignment feature 116 includes a protrusion extending from a top surface of the base 110 that corresponds to a corner of the box 122, such that when the corner of the box 122 is seated against the corresponding structure of the alignment feature 116, the opening 126 of the box 122 of the sterilizable container 120 is disposed above or otherwise aligned with the source coil 112 of the base 110, thereby aiding in the positioning of the sterilizable container 120 on the base 110 for power transfer. In other examples, various other alignment features are contemplated, including, but not limited to, one or more ribs or other features sized, shaped, or otherwise configured to allow the sterilizable container 120 to be seated thereon or therewithin in order to align the sterilizable container 120 with respect to the source coil 112. In other examples, the alignment feature can include one or more grooves sized, shaped, or otherwise configured to allow the sterilizable container 120 to be seated within the one or more grooves in order to align the sterilizable container 120 with respect to the source coil 112. In still other examples, the base 110 can include one or more markings on the base 110 to facilitate alignment of the sterilizable container 120 with respect to the source coil 112.

In some examples, a repeater coil assembly 150 is disposed within the opening 126 of the box 122. In some examples, the repeater coil assembly 150 includes a repeater coil 152 attached to an insert 154. The insert 154, in some examples, provides insulation of the repeater coil 152 from the metal of the box 122 (for instance, the bottom 122B of the box 122). In some examples, the material of the insert 154 is non-magnetic and non-conductive, such as, for instance, one or more ceramic materials, one or more epoxies, potting material, or a combination thereof. In some examples, a gap between the repeater coil 152 and the wall of the sterilizable container 120 is wide enough so that the alternating current (AC) voltage that is induced on the repeater coil 152 does not arc across the gap. In various examples, the material properties of the insert 154 determine how good of an insulator it is, thereby driving the size of the gap.

Figure 4:
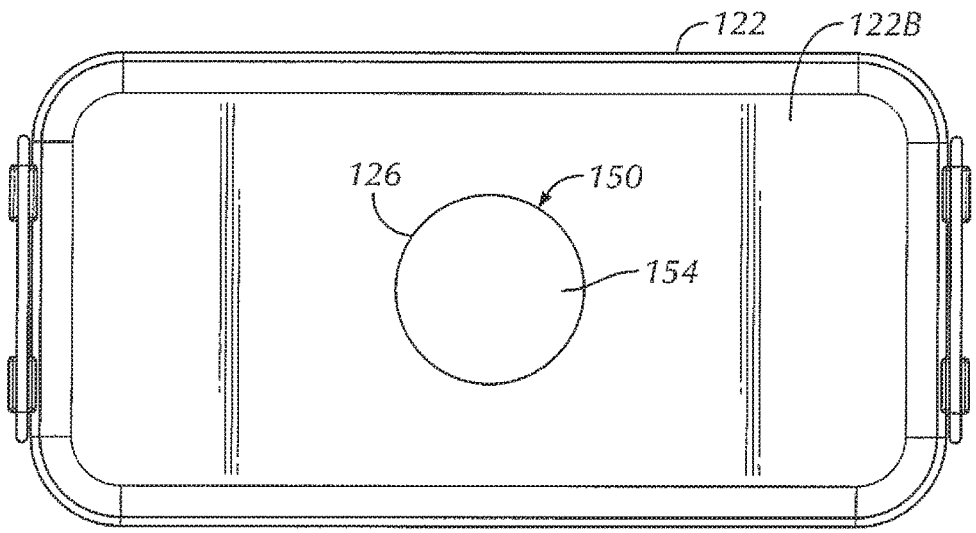
FIG. 4 is a bottom view of the sterilizable container of the system of FIG. 1.
Figure 4A:
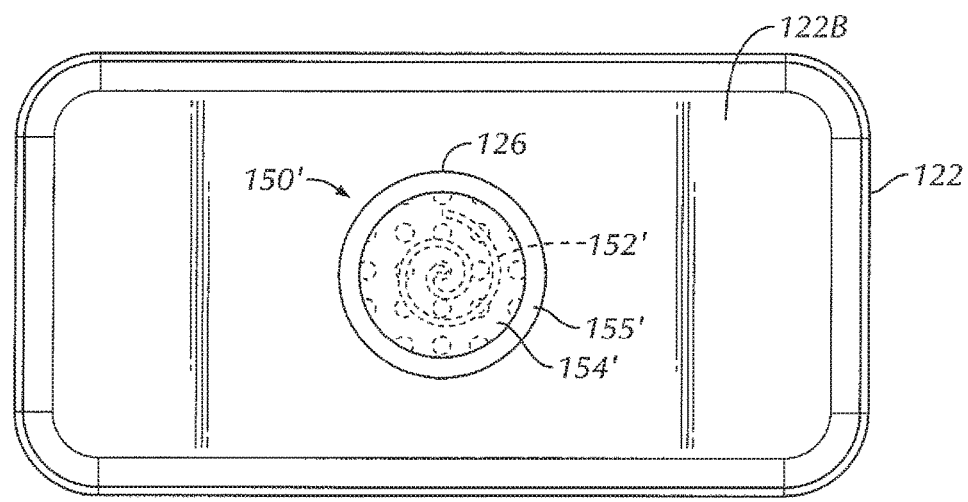
FIG. 4A is a bottom view of the sterilizable container of the system of FIG. 1 with an alternate coil assembly.
Figure 5:
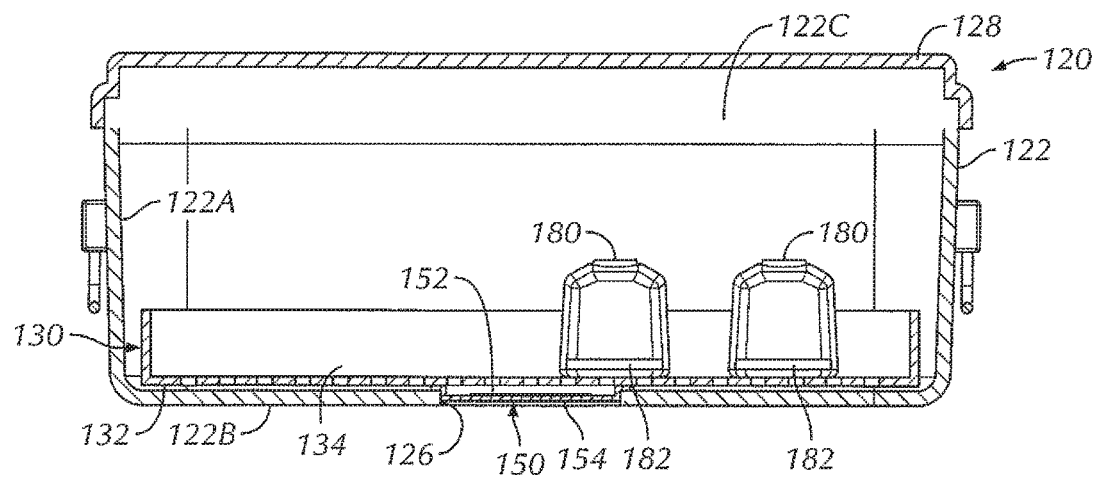
FIG. 5 is a cross-sectional view of the sterilizable container of the system of FIG. 1.
Figure 5A:
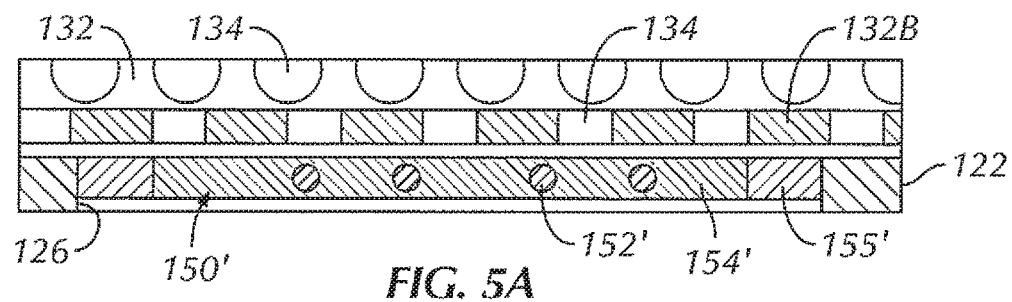
FIG. 5A is a cross-sectional view of the sterilizable container with the alternate coil assembly of FIG. 4A.
Figure 6:
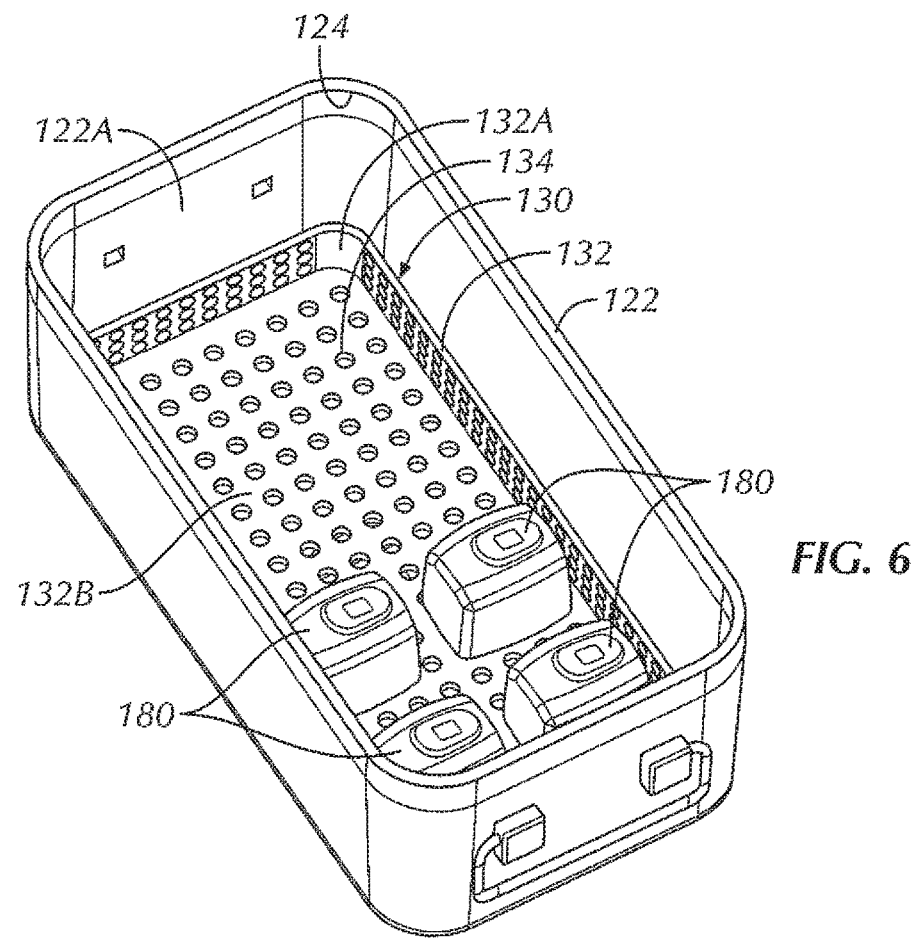
FIG. 6 is a perspective view of the interior of the sterilizable container of the system of FIG. 1.

In some examples, the repeater coil 152 is formed from one or more traces on a circuit board or other substrate. In other examples, the repeater coil includes other configurations, including, but not limited to, a coil disposed within the insert, a coil formed from wire, a coil etched into a substrate or the insert, and/or a combination thereof. For instance, referring briefly to FIGS. 4A and 5A, in some examples, a repeater coil assembly 150' is disposed within the opening 126 of the box 122. In some examples, the repeater coil assembly 150' includes a repeater coil 152' which is disposed within an insert 154'. The insert 154', in some examples, provides at least some insulation of the repeater coil 152' from the metal of the box 122 (for instance, the bottom 122B of the box 122). In some examples, the insert 154' includes potting material, such that the repeater coil 152' is potted within the repeater coil assembly 150'. In this way, the repeater coil 152' can be fully encapsulated, thereby insulating the repeater coil 152' from electrically arcing with the wall of the sterilizable container 120. In some examples, an insulative layer 155' is disposed between the insert 154' and the box 122. In some examples, the insulative layer 155' is formed from an insulative material configured to provide at least some electrically isolation between the box 122 and the repeater coil 152' and/or the insert 154'. In various examples, the insulative layer 155' can be formed from various materials, including, but not limited to a ceramic material, a plastic material, an elastomeric material, potting material, or the like, or a combination thereof. In some examples, the repeater coil assembly 150' allows the electromagnetic field to pass through the potted area of the insert 154' while the insulative layer 155' inhibits, if not eliminates, interference from the metal of the box 122. In some examples, a number of layers of potting material of the insert 154' and/or the thickness of the insulative layer 155' can be increased or decreased to optimize the electromagnetic field.

In some examples, the size of the repeater coil 152 depends on how far away from the source coil 112 the repeater coil 152 is. The size of the repeater coil 152 can also be varied, in some examples, depending upon the number, type, and/or size of the electrical devices that are intended to be wirelessly powered within the sterilizable container 120. In some examples, the repeater coil 152 can be formed from the same conductive material as the sterilizable container 120, such as, but not limited to aluminum, stainless steel, or the like. In other examples, the repeater coil 152 can be formed from copper, to provide a relatively low cost material for the repeater coil 152 with desirable electrical and mechanical performance.

The coil assembly 150, in some examples, is affixed within the opening 126 of the box 122. In various examples, various methods of affixation of the coil assembly 150 include, but are not limited to, fastening using one or more screws or other fasteners, affixation using one or more adhesives, affixation using a welding technique (laser, ultrasonic, or the like), affixation by molding of the insert 154 or other portion of the coil assembly 150 directly within the opening 126 and to the box 122, or the like. In some examples, the repeater coil assembly 150 is affixed within the opening 126 to seal the opening 126 of the box 122 in order to maintain a sterile barrier after the interior 122C of the sterile container 120 and the contents within the interior 122C have been autoclaved or otherwise sterilized. In some examples, a thickness of the repeater coil assembly 150 is substantially similar to a thickness of the box 122 (for instance, a thickness of the bottom 122B of the box 122). In this way, an outer surface of the box 122 is substantially uniform and/or free of protrusions that could make stacking of the sterilizable container 120 with other sterilizable containers problematic and/or could potentially interfere with the autoclave, thereby inhibiting the sterilizable container 120 from being sterilized in the same autoclave as standard sterilizable containers.

The repeater coil 152, in some examples, is configured to receive electromagnetic waves from the source coil 112 and retransmits the electromagnetic waves within the sterilizable container 120. The repeater coil 152, in some examples, is tuned with respect to the source coil 112 in order to efficiently receive electromagnetic waves from the source coil 112. In some examples, a capacitor can be used with the repeater coil 152 in order to tune the repeater coil 152. That is, in some examples, a capacitor can be connected in parallel with a connection of the repeater coil 152, and a value of the capacitor can be such that the repeater coil 152 has a resonant frequency at a specific frequency. In some examples, an inductor value of the repeater coil 152 and/or a target frequency can dictate the value of the capacitor. In some examples, the capacitor can be chosen to have a voltage of the capacitor high enough to handle the energy being transferred. In some examples, the capacitor can be chosen to have a temperature rating that is high enough to survive the temperatures during the autoclave or other sterilization process. In some examples, the capacitor can be chosen to have a low equivalent series resistance (ESR) in order to reduce loses from the capacitor.

In various examples, the capacitor can be located in various locations with respect to the sterilizable container 120. For instance, in some examples, the capacitor can be located on an exterior of the sterilizable container 120. However, such a configuration includes a risk of being damaged due to the outside of the sterilizable container 120 coming into direct contact with a user and/or external objects (such as, but not limited to other sterilizable containers, an autoclave device, shelves, or the like, to name a few). In some examples, the capacitor can be located within the interior 122C of the sterilizable container 120. In some examples, the capacitor can be located next to the repeater coil 152, if the thickness of the capacitor is less than a thickness of the wall of the sterilizable container 120. Such a configuration can be advantageous in that it can reduce the risk of contacting and/or damaging the capacitor from inside of the sterilizable container 120 or outside of the sterilizable container 120, yet it can still provide a parallel connection of the capacitor to the repeater coil 152 built into the sterilizable container 120.

In some examples, the electromagnetic waves retransmitted by the repeater coil 152 are received by a receiving coil 182 affixed to each of the one or more electrical devices 180. In some examples, the receiving coil 182 is disposed within each of the one or more electrical devices 180. In some examples, the receiving coil 182 is tuned with respect to the source coil 112 and/or repeater coil 152 in order to efficiently receive electromagnetic waves from the repeater coil 152.

In this way, in some examples, with the one or more electrical devices 180 disposed within the sterilizable container 120, power can be transferred from the source coil 112 of the base 110, through the box 122 (for instance, through the bottom 122B of the box 122), and into the interior 122C of the box 122 to be received by the receiving coil 182 of each of the one or more electrical devices 180 in order to wirelessly power the one or more electrical devices 180. In some examples, the one or more electrical devices 180 include one or more batteries 180 configured to be wirelessly charged by the base 110. That is, in some examples, the system 100 is configured to wirelessly charge the one or more batteries 180 within the sterilizable container 120. Furthermore, in some examples, the repeater coil 152 allows for power to be transferred through the box 122 (for instance, through the bottom 122B of the box 122) with little to no obstruction from the box 122.

In some examples, with the component tray 130 being used within the sterilizable container 120 during wireless powering, it is possible that the component tray 130 can interfere with the wireless transfer of power between the base 110 and the one or more electrical devices 180 since a portion of the component tray 130 (for instance, the bottom 132B of the component tray 130) would be disposed in between the base 110 and the one or more electrical devices 180. For this reason, the component tray 130, in various examples, can be configured to limit, if not eliminate, interference and/or obstruction with the wireless transfer of power. For instance, in some examples, the component tray 130 includes an insert 136 formed from a material that allows electromagnetic waves to pass through more efficiently than a metallic material. In some examples, the insert 136 can be formed from a polymeric material. In further examples, the insert 136 can be formed from a plastic material. In other examples, the insert 136 can be formed from other materials that allow electromagnetic waves to pass through with little to no interference, such as, but not limited to, glass, ceramic, or the like. In other examples, the component tray 130 can include openings in the tray portion 132, the openings being configured to allow for electromagnetic waves to pass therethrough. In some examples, the holes or openings 134 can be configured to allow for efficient passage of electromagnetic waves therethrough. In further examples, the tray portion 132 can include openings that are shaped differently from the openings 134 shown in FIGS. 2 and 6 to further enhance the efficiency of the passage of electromagnetic waves through the tray portion 132. For instance, in some examples, one or more of the openings can include an elongated shape (rectangular or elliptical, for instance) or a larger diameter than that of the openings 134. That is, in various embodiments, variously shaped openings of the tray portion 132 are contemplated herein, provided the openings provide for relatively efficient transfer of power through the component tray 130 between the source coil 112 of the base 110 and the receiving coil 182 of the one or more electrical devices 180.

The examples of the system 100 allow for wireless power transfer from the base 110 to the one or more electrical devices 180 disposed within the sterilizable container 120 via the source coil 112 within the base 110, the repeater coil 152 within a wall of the box 122 of the sterilizable container 120, and the receiving coil 182 within each of the one or more electrical devices 180. In this way, the sterile field within the sterilizable container 120 can be maintained because the sterile barrier of the sterilizable container 120 is not breached, and the one or more electrical devices 180 are able to be immersively sterilized in that the one or more electrical devices 180 are wirelessly powered and do not require the one or more electrical devices to be plugging in, potentially obstructing at least a portion of the one or more electrical devices 180 from being fully sterilized.

Although the system 100 of FIGS. 1-6 is shown with a sterilizable container 120, the base 110 of the system 100 can also be used with other types of sterilizable vessels. For instance, in some examples, the base 110 can be used with a tray similar to the tray 720 of FIGS. 7-9, but modified in a manner consistent with the examples of the sterilizable container 120 described above. Specifically, in some examples, the tray 720 modified for use with the base 110 can include an opening in a bottom of the bottom portion 722 similar to the opening 126 of the box 122 of the sterilizable container 120 described above, within which can be disposed a repeater coil assembly similar to the repeater coil assembly 150. In some examples, if the component tray 730 is to be used with the modified tray, the component tray 730 can include an insert similar to the insert 136 described above and/or include openings in the component tray 730 configured to allow electromagnetic waves to pass through the component tray 730 with little to no interference caused by the component tray 730. Also, each of the one or more electrical devices 780, in some examples, can include a receiving coil similar to the receiving coil 182 described above. In this way, a modified tray can be used for wireless power transfer to one or more electrical devices 780 disposed within the tray without breaking the sterile field created within the antimicrobial wrap 740 after an autoclave process or other sterilization procedure of the modified tray and the one or more electrical devices 780 disposed within the modified tray. In some examples, the one or more electrical devices 780 include one or more batteries 780 that are configured to be wirelessly charged by electromagnetic waves generated by the source coil 112 of the base 110, in a manner similar to that which is described above with respect to the system 100.

Referring to FIGS. 10-13, in some examples, a system 1000 is configured to wirelessly power an electrical device 1080 within a sterilizable vessel 1020. In some examples, an interior of the sterilizable vessel 1020 is sized and shaped to accommodate at least one electrical device 1080 within the interior of the sterilizable vessel 1020. In some examples, as will be described in more detail herein, a power generating device 1010 is configured to generate and transfer power to the electrical device 1080. In some examples, the sterilizable vessel 1020 is configured to accommodate the electrical device 1080, the sterilizable vessel 1020 being configured to allow power to be at least partially wirelessly transferred from the power generating device 1010, through the sterilizable vessel 1020, and to the electrical device 1080.

The sterilizable vessel 1020, in some examples, includes a sterilizable container 1020. In various examples, the sterilizable container 1020 can be formed from a metallic material. For instance, in some examples, the sterilizable container 1020 can be formed from stainless steel. In other examples, the sterilizable container 1020 can be formed from aluminum. In some examples, the sterilizable container 1020 includes a box 1022 including sidewalls 1022A and a bottom 1022B, the box 1022 including an opening 1024 to access an interior 1022C of the box 1022. In some examples, the opening 1024 is in a top of the box 1022. The sterilizable container 1020, in some examples, includes a closure or lid 1028 that, when in a closed position (FIGS. 10-12), seals the opening 1024 and the interior 1022C of the box 1022. A portion of the sterilizable container 1020, in some examples, includes an antimicrobial filter 1029 configured to allow heat and steam within the sterilizable container 1020 with the lid 1028 closed (for instance, during an autoclave process) but not allow contaminants into the sterilizable container 1020 in order to maintain a sterile environment within the sterilizable container 1020. In some examples, the antimicrobial filter 1029 is disposed within the lid 1028. In other examples, an antimicrobial filter can be disposed within one or more of the sidewalls 1022A of the box 1022 and/or the bottom 1022B of the box 1022.

Within the interior 1022C of the sterilizable container 1020, in some examples, is a component tray 1030 configured to hold one or more components, such as one or more electrical devices 1080, within the sterilizable container 1020 for sterilization. In some examples, the component tray 1030 is removable from within the interior 1022C of the sterilizable container 1020. In some examples, the component tray 1030 includes a tray portion 1032 having sidewalls 1032A and a bottom 1032B, the tray portion 1032 defining an interior 1032C configured to hold one or more components therein, for instance, during an autoclave process or other sterilization procedure. In some examples, at least a portion of the tray portion 1032 includes holes or openings 1034 therethrough to allow steam and/or heat from the autoclave process or other sterilization procedure to penetrate the interior 1032C of the tray portion 1032 and envelop the one or more components in order to sterilize the one or more components. In some examples, the component tray 1030 is sized and shaped to freely slide into and out of the interior 1022B of the box 1022, for example, when a user is inserting the component tray 1030 into the box 1022 and taking the component tray 1030 out of the box 1022, for instance, to insert or remove one or more components (such as one or more electrical devices 1080). In some examples, the bottom 1032B of the component tray 1030 is configured to rest at least a distance from the bottom 1022B of the box. In this way, in some examples, the distance allows for the one or more components to rest spaced from the bottom 1022B of the box 1022 in the event that excess heat builds up at the bottom 1022B of the box 1022 or condensation and/or water pools at the bottom 1022B of the box 1022, so as to decrease the chances that the one or more components become damaged by excessive heat and/or by becoming at least partially submerged in pooling water.

In some examples, the system 1000 includes the power generating device 1010. In some examples, the power generating device 1010 is a base 1010 that is sized and shaped to allow a sterilizable container 1020 to be placed on top of the base 1010. The base 1010, in some examples, is connectable to power, such as, but not limited to, by plugging a power cord 1014 of the base 1010 into a wall outlet. The base 1010 includes, in various examples, contacts 1012 disposed on a surface so as to be in proximity to the sterilizable container 1020 with the sterilizable container 1020 being situated on or otherwise in place with respect to the base 1010. The contacts 1012, in some examples, are configured to make electrical contact with like contacts and transfer power through this connection. In some examples, it is contemplated that the base 1010 also include a source coil positioned within the base 1010, the source coil being similar to the source coil 112 described above with respect to the system 100, such that the base 1010 would be able to transfer power with a direct connection via the contacts 1012, as well as with a wireless connection via the source coil, in a manner similar to that described above with respect to the system 100. In this way, the base 1010 can be used to transfer power to components within various types of sterilizable containers (such as sterilizable containers 120, 1020).

In some examples, the sterilizable container 1020 includes an aperture or opening 1026 in the box 1022. In some examples, the opening 1026 is disposed within the bottom 1022B of the box 1022, although in other examples, the opening can be disposed within other portions of the box 1022, depending upon the positioning of the contacts 1012 of the base 1010. In some examples, the opening 1026 of the sterilizable container 1020 is positioned to be aligned with the contacts 1012 of the base 1010 with the sterilizable container 1020 in position for power transfer on the base 1010.

In some examples, a coil assembly 1050 is disposed within the opening 1026 of the box 1022. In some examples, the coil assembly 1050 includes contacts 1056 and a source coil 1052 attached to an insert 1054. The insert 1054, in some examples, provides insulation of the contacts 1056 and the source coil 1052 from the metal of the box 1022 (for instance, the bottom 1022B of the box 1022). In some examples, the contacts 1056 are positioned on the insert 1054 such that the contacts 1056 align with and abut the contacts 1012 of the base 1010 with the sterilizable container 1020 in place on the base 1010. In some examples, the contacts 1056 are spring-loaded to allow the contacts 1056 to depress when abutted by another surface, such as when placed down upon the contacts 1012 of the base 1010, but be biased back outwardly when not in contact with another surface. In this way, a proper connection is facilitated between the contacts 1056 and another surface (such as, but not limited to the contacts 1012 of the base 1010). For instance, such spring-loaded contacts 1056 can include Pogo pins, in some examples. In other examples, various other types of contacts 1056 are contemplated herein, including, but not limited to, rigid conductive pads, leaf springs, coil springs, prongs, hinged contacts, and/or a combination thereof.

In some examples, the contacts 1056 are electrically connected to the source coil 1052, such that, with the contacts 1056 of the coil assembly 1050 electrically coupled to the contacts 1012 of the base 1010, the source coil 1052 can be powered by the base 1010. In some examples, the source coil 1052 is formed from one or more traces on a circuit board or other substrate. In other examples, the source coil includes other configurations, including, but not limited to, a coil disposed within the insert, a coil formed from wire, a coil etched into a substrate or the insert, and/or a combination thereof. In some examples, the coil assembly 1050 can be similar to the coil assembly 150' of FIGS. 4A and 5A. In some examples, the size of the source coil 1052 depends on how far away from the source coil 1052 is from the one or more electrical devices to be wirelessly powered. The size of the source coil 1052 can also be varied, in some examples, depending upon the number, type, and/or size of the electrical devices that are intended to be wirelessly powered within the sterilizable container 1020. In various examples, the source coil 1052 can be formed from aluminum, stainless steel, or the like. In other examples, the source coil 1052 can be formed from copper, to provide a relatively low cost material for the source coil 1052 with desirable electrical and mechanical performance.

The coil assembly 1050, in some examples, is affixed within the opening 1026 of the box 1022. In various examples, various methods of affixation of the coil assembly 1050 include, but are not limited to, fastening using one or more screws or other fasteners, affixation using one or more adhesives, affixation using a welding technique (laser, ultrasonic, or the like), affixation by molding of the insert 1054 or other portion of the coil assembly 1050 directly within the opening 1026 and to the box 1022, or the like. In some examples, the coil assembly 1050 is affixed within the opening 1026 to seal the opening 1026 of the box 1022 in order to maintain a sterile barrier after the interior 1022C of the sterile container 1020 and the contents within the interior 1022C have been autoclaved or otherwise sterilized. In some examples, a thickness of the coil assembly 1050 is substantially similar to a thickness of the box 1022 (for instance, a thickness of the bottom 1022B of the box 1022). In this way, an outer surface of the box 1022 is substantially uniform and/or free of protrusions that could make stacking of the sterilizable container 1020 with other sterilizable containers problematic and/or could potentially interfere with the autoclave, thereby inhibiting the sterilizable container 1020 from being sterilized in the same autoclave as standard sterilizable containers.

The source coil 1052, in some examples, is configured transmit electromagnetic waves within the sterilizable container 1020 in order to wirelessly power the one or more electrical devices 1080. In some examples, the electromagnetic waves transmitted by the source coil 1052 are received by a receiving coil affixed to each of the one or more electrical devices 1080, in a manner similar to that described above with respect to the receiving coil 182 of the electrical device 180. In some examples, the receiving coil is disposed within each of the one or more electrical devices 1080. In some examples, the receiving coil is tuned with respect to the source coil 1052 in order to efficiently receive electromagnetic waves from the source coil 1052. In some examples, a capacitor can be placed in series with the source coil 1052, the source coil 1052 having the direct connection from the base 1010. In this way, the source coil 1052 can be tuned to match a specific resonant frequency to efficiently transfer power between the source coil 1052 and the receiving coil of the one or more electrical devices 1080. In further examples, the capacitor can be disposed within the base 1010, thereby decreasing the chances of damaging the capacitor and improving the reliability of the system 1000.

In this way, in some examples, with the one or more electrical devices 1080 disposed within the sterilizable container 1020, the source coil 1052 can be powered by the base 1010 via the interacting contacts 1012, 1056, and the source coil 1052 can transmit electromagnetic waves within the sterilizable container 1020 to be received by the receiving coil of each of the one or more electrical devices 1080 in order to wirelessly power the one or more electrical devices 1080. In some examples, the one or more electrical devices 1080 include one or more batteries 1080 configured to be wirelessly charged by the source coil 1052. That is, in some examples, the system 1000 is configured to wirelessly charge the one or more batteries 1080 within the sterilizable container 1020. Furthermore, in some examples, the contacts 1012, 1056 allow for power to be transferred through the box 1022 (for instance, via the interacting contacts 1012, 1056) with little to no obstruction from the box 1022.

In some examples, with the component tray 1030 being used within the sterilizable container 1020 during wireless powering, it is possible that the component tray 1030 can interfere with the wireless transfer of power between the source coil 1052 and the one or more electrical devices 1080 since a portion of the component tray 1030 (for instance, the bottom 1032B of the component tray 1030) would be disposed in between the source coil 1052 and the one or more electrical devices 1080. For this reason, the component tray 1030, in various examples, can be configured to limit, if not eliminate, interference and/or obstruction with the wireless transfer of power. For instance, in some examples, the component tray 1030 includes an insert 1036 formed from a material that allows electromagnetic waves to pass through more efficiently than a metallic material. In some examples, the insert 1036 can be formed from a polymeric material. In further examples, the insert 1036 can be formed from a plastic material. In other examples, the insert 1036 can be formed from other materials that allow electromagnetic waves to pass through with little to no interference, such as, but not limited to, glass, ceramic, or the like. In other examples, the component tray 1030 can include openings in the tray portion 1032, the openings being configured to allow for electromagnetic waves to pass therethrough. In some examples, the holes or openings 1034 can be configured to allow for efficient passage of electromagnetic waves therethrough. In further examples, the tray portion 1032 can include openings that are shaped differently from the openings 1034 shown in FIG. 13 to further enhance the efficiency of the passage of electromagnetic waves through the tray portion 1032. For instance, in some examples, one or more of the openings can include an elongated shape (rectangular or elliptical, for instance) or a larger diameter than that of the openings 1034. That is, in various embodiments, variously shaped openings of the tray portion 1032 are contemplated herein, provided the openings provide for relatively efficient transfer of power through the component tray 1030 between the source coil 1052 of the coil assembly 1050 and the receiving coil of the one or more electrical devices 1080.

The examples of the system 1000 allow for a direct connection of the base 1010 and the coil assembly 1050 via the contacts 1012 of the base 1010 interacting with the contacts 1056 of the coil assembly 1050 and allow for the wireless transfer of power within the sterilizable container 1020 between the source coil 1052 and the coil in the one or more electrical devices 1080. In this way, the sterile field within the sterilizable container 1020 can be maintained because the sterile barrier of the sterilizable container 1020 is not breached, and the one or more electrical devices 1080 are able to be immersively sterilized in that the one or more electrical devices 1080 are wirelessly powered and do not require the one or more electrical devices to be plugging in, potentially obstructing at least a portion of the one or more electrical devices 1080 from being fully sterilized.

Figure 14:
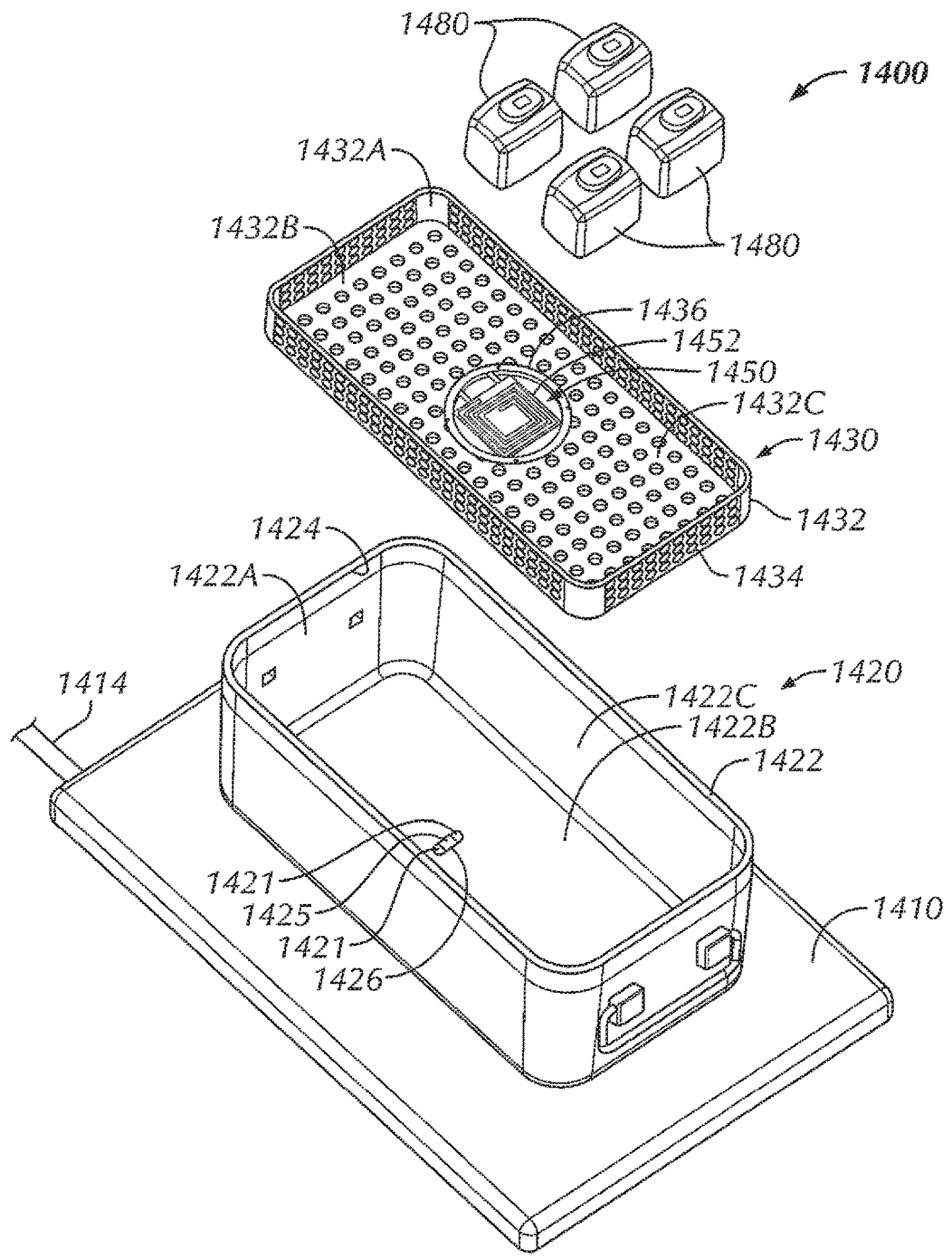
FIG. 14 is an exploded view of a system in accordance with at least one example of the invention.
Figure 15:
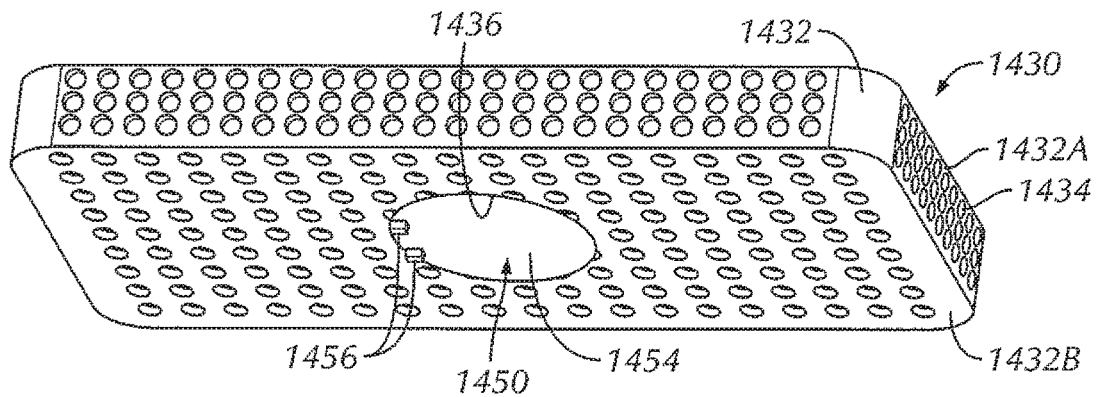
FIG. 15 is a perspective view of a bottom of a component tray of a sterilizable container of the system of FIG. 14.

Referring to FIGS. 14 and 15, in some examples, a system 1400 is configured to wirelessly power an electrical device 1480 within a sterilizable vessel 1420. In some examples, an interior of the sterilizable vessel 1420 is sized and shaped to accommodate at least one electrical device 1480 within the interior of the sterilizable vessel 1420. In some examples, as will be described in more detail herein, a power generating device 1410 is configured to generate and transfer power to the electrical device 1480. In some examples, the sterilizable vessel 1420 is configured to accommodate the electrical device 1480, the sterilizable vessel 1420 being configured to allow power to be at least partially wirelessly transferred from the power generating device 1410, through the sterilizable vessel 1420, and to the electrical device 1480.

The sterilizable vessel 1420, in some examples, includes a sterilizable container 1420. In various examples, the sterilizable container 1420 can be formed from a metallic material. For instance, in some examples, the sterilizable container 1420 can be formed from stainless steel. In other examples, the sterilizable container 1420 can be formed from aluminum. In some examples, the sterilizable container 1420 includes a box 1422 including sidewalls 1422A and a bottom 1422B, the box 1422 including an opening 1424 to access an interior 1422C of the box 1422. In some examples, the opening 1424 is in a top of the box 1422. Although not shown in FIGS. 14 and 15, the sterilizable container 1420, in some examples, includes a closure or lid that, when in a closed position, seals the opening 1424 and the interior 1422C of the box 1422. In some examples, the lid of the sterilizable container 1420 is similar to the lids 128, 1028 described above. A portion of the sterilizable container 1420, in some examples, includes an antimicrobial filter configured to allow heat and steam within the sterilizable container 1420 with the lid closed (for instance, during an autoclave process) but not allow contaminants into the sterilizable container 1420 in order to maintain a sterile environment within the sterilizable container 1420. In some examples, the antimicrobial filter is disposed within the lid. In other examples, an antimicrobial filter can be disposed within one or more of the sidewalls 1422A of the box 1422 and/or the bottom 1422B of the box 1422.

Within the interior 1422C of the sterilizable container 1420, in some examples, is a component tray 1430 configured to hold one or more components, such as one or more electrical devices 1480, within the sterilizable container 1420 for sterilization. In some examples, the component tray 1430 is removable from within the interior 1422C of the sterilizable container 1420. In some examples, the component tray 1430 includes a tray portion 1432 having sidewalls 1432A and a bottom 1432B, the tray portion 1432 defining an interior 1432C configured to hold one or more components therein, for instance, during an autoclave process or other sterilization procedure. In some examples, at least a portion of the tray portion 1432 includes holes or openings 1434 therethrough to allow steam and/or heat from the autoclave process or other sterilization procedure to penetrate the interior 1432C of the tray portion 1432 and envelop the one or more components in order to sterilize the one or more components. In some examples, the component tray 1430 is sized and shaped to freely slide into and out of the interior 1422B of the box 1422, for example, when a user is inserting the component tray 1430 into the box 1422 and taking the component tray 1430 out of the box 1422, for instance, to insert or remove one or more components (such as one or more electrical devices 1480). In some examples, the bottom 1432B of the component tray 1430 is configured to rest at least a distance from the bottom 1422B of the box. In this way, in some examples, the distance allows for the one or more components to rest spaced from the bottom 1422B of the box 1422 in the event that excess heat builds up at the bottom 1422B of the box 1422 or condensation and/or water pools at the bottom 1422B of the box 1422, so as to decrease the chances that the one or more components become damaged by excessive heat and/or by becoming at least partially submerged in pooling water.

In some examples, the system 1400 includes the power generating device 1410. In some examples, the power generating device 1410 is a base 1410 that is sized and shaped to allow a sterilizable container 1420 to be placed on top of the base 1410. The base 1410, in some examples, is connectable to power, such as, but not limited to, by plugging a power cord 1414 of the base 1410 into a wall outlet. The base 1410 includes, in various examples, contacts (although not shown in FIG. 14, the contacts can be similar to contacts 1012 of system 1000 described above) disposed on a surface so as to be in proximity to the sterilizable container 1420 with the sterilizable container 1420 being situated on or otherwise in place with respect to the base 1410. The contacts, in some examples, are configured to make electrical contact with like contacts and transfer power through this connection. In some examples, it is contemplated that the base 1410 also include a source coil positioned within the base 1410, the source coil being similar to the source coil 112 described above with respect to the system 100, such that the base 1410 would be able to transfer power with a direct connection via the contacts, as well as with a wireless connection via the source coil, in a manner similar to that described above with respect to the system 100. In this way, the base 1410 can be used to transfer power to components within various types of sterilizable containers (such as sterilizable containers 120, 1020, 1420).

In some examples, the sterilizable container 1420 includes contacts 1421 disposed within a wall of the box 1422. In some examples, the contacts 1421 are disposed within one or more openings 1426 in the box 1422. In some examples, an insulative layer 1425 is disposed between the contacts 1421 and the box 1422 in order to electrically insulate the contacts 1421 from the metal of the box 1422. In some examples, the opening 1426 is disposed within the bottom 1422B of the box 1422, although in other examples, the opening can be disposed within other portions of the box 1422, depending upon the positioning of the contacts of the base 1410. In some examples, the opening 1426 of the sterilizable container 1420 is positioned to be aligned with the contacts of the base 1410 with the sterilizable container 1420 in position for power transfer on the base 1410.

In some examples, a coil assembly 1450 is disposed within an opening 1436 of the component tray 1430. In some examples, the coil assembly 1450 includes contacts 1456 and a source coil 1452 attached to an insert 1454. The insert 1454, in some examples, provides insulation of the contacts 1456 and the source coil 1452 from the metal of the component tray 1430 (for instance, the bottom 1432B of the tray portion 1432). In some examples, the contacts 1456 are positioned on the insert 1454 such that the contacts 1456 align with and abut the contacts 1421 of the box 1422 with the component tray 1430 in place within the box 1422 of the sterilizable container 1420. In some examples, the contacts 1456 are spring-loaded to allow the contacts 1456 to depress when abutted by another surface, such as when placed down upon the contacts 1421 of the box 1422, but be biased back outwardly when not in contact with another surface. In this way, a proper connection is facilitated between the contacts 1456 and another surface (such as, but not limited to the contacts 1421 of the box 1422). For instance, such spring-loaded contacts 1556 can include Pogo pins, in some examples. In other examples, various other types of contacts 1556 are contemplated herein, including, but not limited to, rigid conductive pads, leaf springs, coil springs, prongs, hinged contacts, and/or a combination thereof.

In some examples, the contacts 1456 are electrically connected to the source coil 1452, such that, with the contacts 1456 of the coil assembly 1450 electrically coupled to the contacts 1421 of the box 1422, the source coil 1452 can be powered by the contacts of the box 1422, which are, in turn, powered by the base 1410. In some examples, the source coil 1452 is formed from one or more traces on a circuit board or other substrate. In other examples, the source coil includes other configurations, including, but not limited to, a coil disposed within the insert, a coil formed from wire, a coil etched into a substrate or the insert, and/or a combination thereof. In some examples, the coil assembly 1450 can be similar to the coil assembly 150' of FIGS. 4A and 5A. In some examples, the size of the source coil 1452 depends on how far away the source coil 1452 is from the one or more electrical devices to be wirelessly powered. The size of the source coil 1452 can also be varied, in some examples, depending upon the number, type, and/or size of the electrical devices that are intended to be wirelessly powered within the sterilizable container 1420. In various examples, the source coil 1452 can be formed from aluminum, stainless steel, or the like. In other examples, the source coil 1452 can be formed from copper, to provide a relatively low cost material for the source coil 1452 with desirable electrical and mechanical performance.

The coil assembly 1450, in some examples, is affixed within the opening 1436 of the component tray 1430. In various examples, various methods of affixation of the coil assembly 1450 include, but are not limited to, fastening using one or more screws or other fasteners, affixation using one or more adhesives, affixation using a welding technique (laser, ultrasonic, or the like), affixation by molding of the insert 1454 or other portion of the coil assembly 1450 directly within the opening 1436 and to the component tray 1430, or the like. In some examples, a thickness of the coil assembly 1450 is substantially similar to a thickness of the component tray 1430 (for instance, a thickness of the bottom 1432B of the component tray 1430).

The source coil 1452, in some examples, is configured to transmit electromagnetic waves within the sterilizable container 1420 in order to wirelessly power the one or more electrical devices 1480. In some examples, the electromagnetic waves transmitted by the source coil 1452 are received by a receiving coil affixed to each of the one or more electrical devices 1480, in a manner similar to that described above with respect to the receiving coil 182 of the electrical device 180. In some examples, the receiving coil is disposed within each of the one or more electrical devices 1480. In some examples, the receiving coil is tuned with respect to the source coil 1452 in order to efficiently receive electromagnetic waves from the source coil 1452. In some examples, a capacitor can be placed in series with the source coil 1452, the source coil 1452 having the direct connection from the base 1410. In this way, the source coil 1452 can be tuned to match a specific resonant frequency to efficiently transfer power between the source coil 1452 and the receiving coil of the one or more electrical devices 1480. In further examples, the capacitor can be disposed within the base 1410, thereby decreasing the chances of damaging the capacitor and improving the reliability of the system 1400.

In this way, in some examples, with the one or more electrical devices 1480 disposed within the sterilizable container 1420, the source coil 1452 can be directly powered by the base 1410 from the base contacts, to the contacts 1421 of the box 1422, to the contacts 1456 of the component tray. Once powered, in some examples, the source coil 1452 can transmit electromagnetic waves within the sterilizable container 1420 to be received by the receiving coil of each of the one or more electrical devices 1480 in order to wirelessly power the one or more electrical devices 1480. In some examples, the one or more electrical devices 1480 include one or more batteries 1480 configured to be wirelessly charged by the source coil 1452. That is, in some examples, the system 1400 is configured to wirelessly charge the one or more batteries 1480 within the sterilizable container 1420. Furthermore, in some examples, the contacts 1421 allow for power to be transferred through the box 1422 (for instance, via the interacting contacts of the base 1410 and contacts 1421, 1456) with little to no obstruction from the box 1422.

The examples of the system 1400 allow for a direct connection of the base 1410 and the coil assembly 1450 via the contacts of the base 1410 and the contacts 1421 of the box 1422 interacting with the contacts 1456 of the coil assembly 1450 and allow for the wireless transfer of power within the sterilizable container 1420 between the source coil 1452 and the coil in the one or more electrical devices 1480. In this way, the sterile field within the sterilizable container 1420 can be maintained because the sterile barrier of the sterilizable container 1420 is not breached, and the one or more electrical devices 1480 are able to be immersively sterilized in that the one or more electrical devices 1480 are wirelessly powered and do not require the one or more electrical devices to be plugging in, potentially obstructing at least a portion of the one or more electrical devices 1480 from being fully sterilized.

Figure 16:
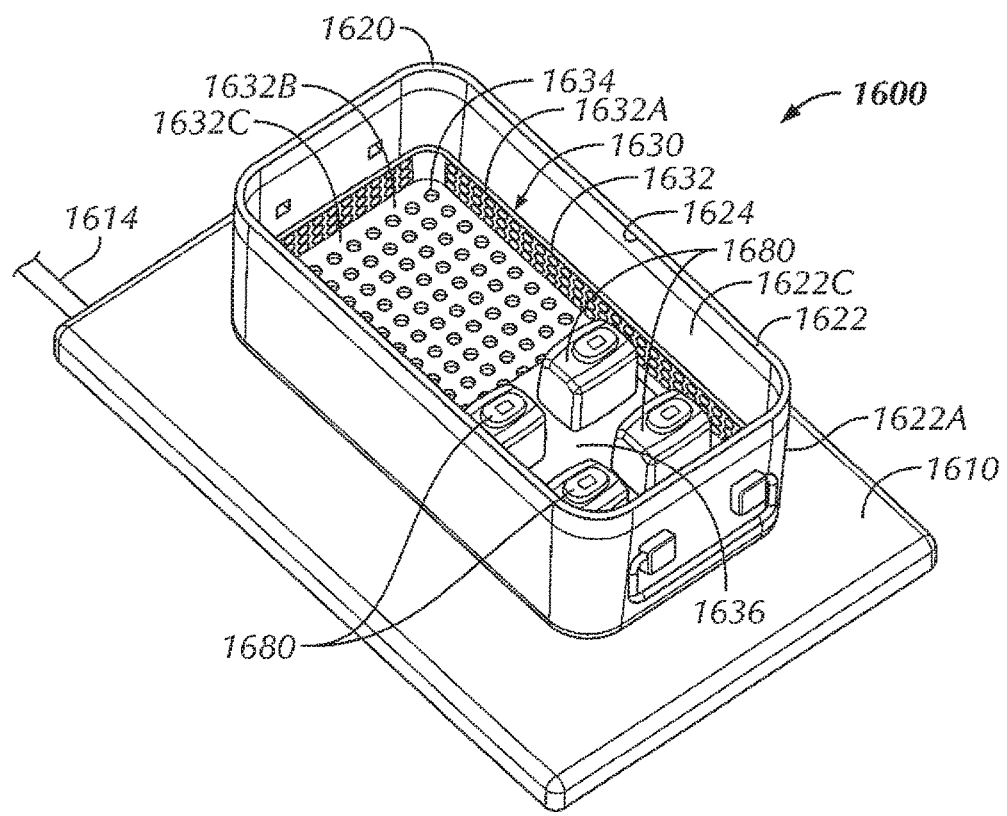
FIG. 16 is a perspective view of a system in accordance with at least one example of the invention.
Figure 17:
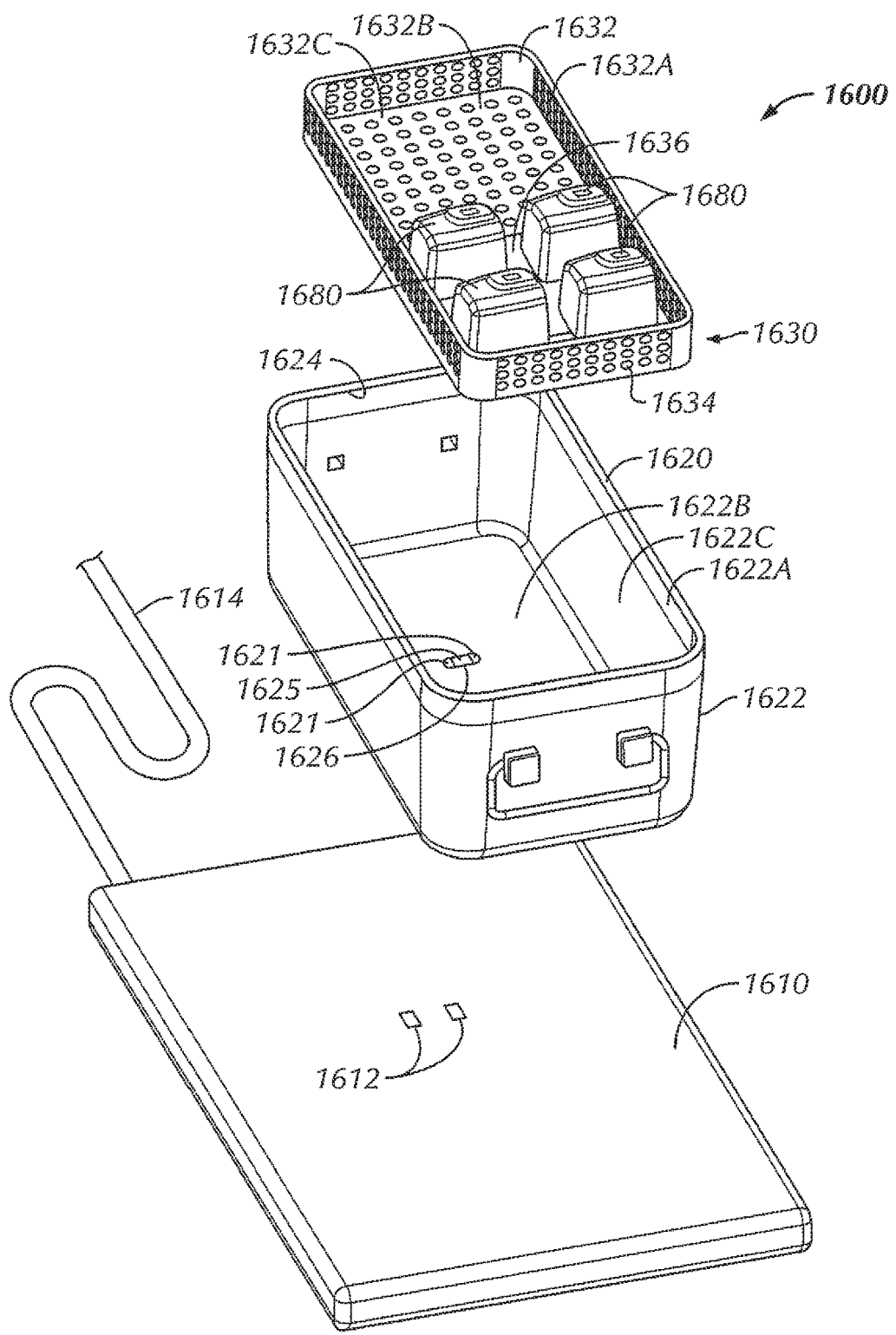
FIG. 17 is an exploded view of the system of FIG. 16.
Figure 18:
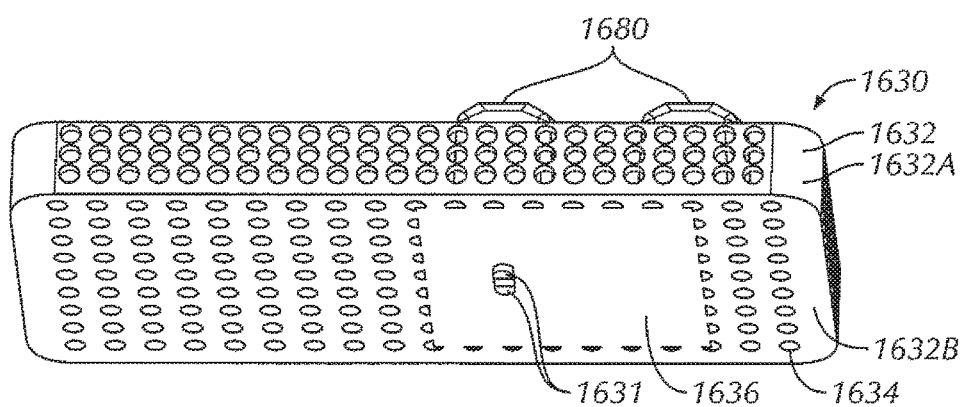
FIG. 18 is a perspective view of a bottom of a component tray of a sterilizable container of the system of FIG. 16.

Referring to FIGS. 16-18, in some examples, a system 1600 is configured to wirelessly power an electrical device 1680 within a sterilizable vessel or container 1620. In some examples, an interior of the sterilizable vessel 1620 is sized and shaped to accommodate at least one electrical device 1680 within the interior of the sterilizable vessel 1620. In some examples, as will be described in more detail herein, a power generating device 1610 is configured to generate and transfer power to the electrical device 1680. In some examples, the sterilizable vessel 1620 is configured to accommodate the electrical device 1680, the sterilizable vessel 1620 being configured to allow power to be at least partially wirelessly transferred from the power generating device 1610, through the sterilizable vessel 1620, and to the electrical device 1680.

The sterilizable vessel 1620, in some examples, includes a sterilizable container 1620. In various examples, the sterilizable container 1620 can be formed from a metallic material. For instance, in some examples, the sterilizable container 1620 can be formed from stainless steel. In other examples, the sterilizable container 1620 can be formed from aluminum. In some examples, the sterilizable container 1620 includes a box 1622 including sidewalls 1622A and a bottom 1622B, the box 1622 including an opening 1624 to access an interior 1622C of the box 1622. In some examples, the opening 1624 is in a top of the box 1622. Although not shown in FIGS. 16-18, the sterilizable container 1620, in some examples, includes a closure or lid that, when in a closed position, seals the opening 1624 and the interior 1622C of the box 1622. In some examples, the lid of the sterilizable container 1620 is similar to the lids 128, 1028 described above. A portion of the sterilizable container 1620, in some examples, includes an antimicrobial filter configured to allow heat and steam within the sterilizable container 1620 with the lid closed (for instance, during an autoclave process) but not allow contaminants into the sterilizable container 1620 in order to maintain a sterile environment within the sterilizable container 1620. In some examples, the antimicrobial filter is disposed within the lid. In other examples, an antimicrobial filter can be disposed within one or more of the sidewalls 1622A of the box 1622 and/or the bottom 1622B of the box 1622.

Within the interior 1622C of the sterilizable container 1620, in some examples, is a component tray 1630 configured to hold one or more components, such as one or more electrical devices 1680, within the sterilizable container 1620 for sterilization. In some examples, the component tray 1630 is removable from within the interior 1622C of the sterilizable container 1620. In some examples, the component tray 1630 includes a tray portion 1632 having sidewalls 1632A and a bottom 1632B, the tray portion 1632 defining an interior 1632C configured to hold one or more components therein, for instance, during an autoclave process or other sterilization procedure. In some examples, at least a portion of the tray portion 1632 includes holes or openings 1634 therethrough to allow steam and/or heat from the autoclave process or other sterilization procedure to penetrate the interior 1632C of the tray portion 1632 and envelop the one or more components in order to sterilize the one or more components. In some examples, the component tray 1630 is sized and shaped to freely slide into and out of the interior 1622B of the box 1622, for example, when a user is inserting the component tray 1630 into the box 1622 and taking the component tray 1630 out of the box 1622, for instance, to insert or remove one or more components (such as one or more electrical devices 1680). In some examples, the bottom 1632B of the component tray 1630 is configured to rest at least a distance from the bottom 1622B of the box. In this way, in some examples, the distance allows for the one or more components to rest spaced from the bottom 1622B of the box 1622 in the event that excess heat builds up at the bottom 1622B of the box 1622 or condensation and/or water pools at the bottom 1622B of the box 1622, so as to decrease the chances that the one or more components become damaged by excessive heat and/or by becoming at least partially submerged in pooling water.

In some examples, the system 1600 includes the power generating device 1610. In some examples, the power generating device 1610 is a base 1610 that is sized and shaped to allow a sterilizable container 1620 to be placed on top of the base 1610. The base 1610, in some examples, is connectable to power, such as, but not limited to, by plugging a power cord 1614 of the base 1610 into a wall outlet. The base 1610 includes, in various examples, contacts 1612 disposed on a surface so as to be in proximity to the sterilizable container 1620 with the sterilizable container 1620 being situated on or otherwise in place with respect to the base 1610. The contacts 1612, in some examples, are configured to make electrical contact with like contacts and transfer power through this connection. In some examples, it is contemplated that the base 1610 also include a source coil positioned within the base 1610, the source coil being similar to the source coil 112 described above with respect to the system 100, such that the base 1610 would be able to transfer power with a direct connection via the contacts, as well as with a wireless connection via the source coil, in a manner similar to that described above with respect to the system 100. In this way, the base 1610 can be used to transfer power to components within various types of sterilizable containers (such as sterilizable containers 120, 1020, 1420, 1620).

In some examples, the sterilizable container 1620 includes contacts 1621 disposed within a wall of the box 1622. In some examples, the contacts 1621 are disposed within one or more openings 1626 in the box 1622. In some examples, an insulative layer 1625 is disposed between the contacts 1621 and the box 1622 in order to electrically insulate the contacts 1621 from the metal of the box 1622. In some examples, the opening 1626 is disposed within the bottom 1622B of the box 1622, although in other examples, the opening can be disposed within other portions of the box 1622, depending upon the positioning of the contacts 1612 of the base 1610. In some examples, the opening 1626 of the sterilizable container 1620 is positioned to be aligned with the contacts 1612 of the base 1610 with the sterilizable container 1620 in position for power transfer on the base 1610.

In some examples, the component tray 1630 includes contacts 1631 disposed within a wall of the tray portion 1632. In some examples, the contacts 1631 extend from a charger 1436 disposed in or on the tray portion 1632. In some examples, the charger 1636 is disposed within the bottom 1632B of the tray portion 1632, although in other examples, the charger can be disposed within other portions of the tray portion 1632, depending upon the positioning of the contacts 1621 of the sterilizable container 1620. In some examples, the contacts 1631 of the charger 1636 are positioned to be aligned with the contacts 1621 of the sterilizable container 1620 with the component tray 1630 in position within the sterilizable container 1620.

In some examples, the contacts 1631 are electrically connected to the charger 1636 of the component tray 1630. In some examples, the charger 1636 includes one or more charging locations in order to charge one or more electrical devices 1680 disposed within the sterilizable container 1620. In some examples, the one or more charging locations include contacts or other electrical attachment or connector configurations corresponding to contacts or other electrical attachment or connector configurations of the one or more electrical devices 1680 to allow the one or more electrical devices 1680 to be electrically coupled to power at the one or more charging locations in order to charge the one or more electrical devices 1680 within the sterilizable container 1620. In some examples, the charger 1636 includes one or more receptacles or nests within a top surface of the charger 1636 in order to facilitate proper placement and location of the one or more electrical devices 1680 within the component tray 1630 in order to align the contacts of the charger with the contacts of the one or more electrical devices 1680 or otherwise efficiently charge the one or more electrical devices 1680.

In this way, in some examples, the one or more electrical devices 1680 disposed within the sterilizable container 1620 can be directly powered by the base 1610 from the base contacts via the contacts 1612, 1621, 1631 interacting and directly electrically connecting the base 1610 to the one or more electrical devices 1680 disposed on the charger 1636 within the sterilizable container 1620. In some examples, the one or more electrical devices 1680 include one or more batteries 1680 configured to be wirelessly charged by the system 1600. That is, in some examples, the system 1600 is configured to directly charge the one or more batteries 1680 within the sterilizable container 1620. Furthermore, in some examples, the contacts 1621 allow for power to be transferred through the box 1622 (for instance, via the interacting contacts 1612 of the base 1610 and contacts 1621, 1631) with little to no obstruction from the box 1622. In this way, in some examples, the system 1600 need not be designed around allowing wireless transfer to pass through the wall of the sterilizable container 1620, thereby potentially allowing the design of the sterilizable container 1920 to remain largely similar to that of other sterilizable containers. Additionally, in some examples, by powering the one or more electrical devices 1680 (for instance, charging batteries 1680) using contacts instead of wireless energy transfer, existing electrical devices 1680 (for instance, batteries 1680) can be used with the system 1600 with very little modification to the sterilizable container 1620.

The examples of the system 1600 allow for a direct electrical connection of the base 1610 and the one or more electrical devices 1680. In this way, the sterile field within the sterilizable container 1620 can be maintained because the sterile barrier of the sterilizable container 1620 is not breached due to the contacts 1621 being sealed within the wall of the box 1622. That is, the contacts 1621 allow for an electrical connection through the wall of the box 1622 but do not allow for contaminants to pass into the sterilizable container 1620, thereby maintaining the sterile field within the sterilizable container 1620.

Although the contacts 1621 of the sterilizable container 1620 are shown as two contacts 1621 disposed within the opening 1626 of the box 1622 and surrounded by the insulating layer 1625, in other examples, different contact configurations of the sterilizable container 1620 (and, in turn, mating contact configurations of the base 1610 and the component tray 1630) are contemplated. For instance, in some examples, the sterilizable container can include only one contact through the wall of the sterilizable container and a portion of the sterilizable container (such as, but not limited to, a portion of the bottom 1622B of the box 1622) can be used as the other contact, such that one contact can act as the positive lead and the other contact can act as the negative lead.

Figure 17A:
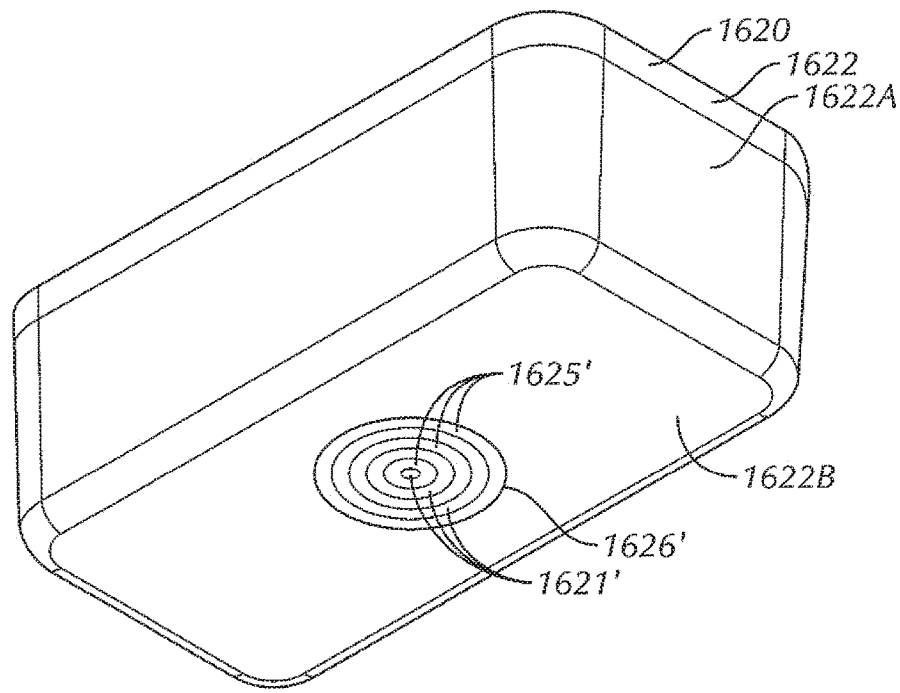
FIG. 17A is a bottom perspective view of the sterilizable container of the system of FIG. 16 with an alternate direct connection configuration.
Figure 17B:
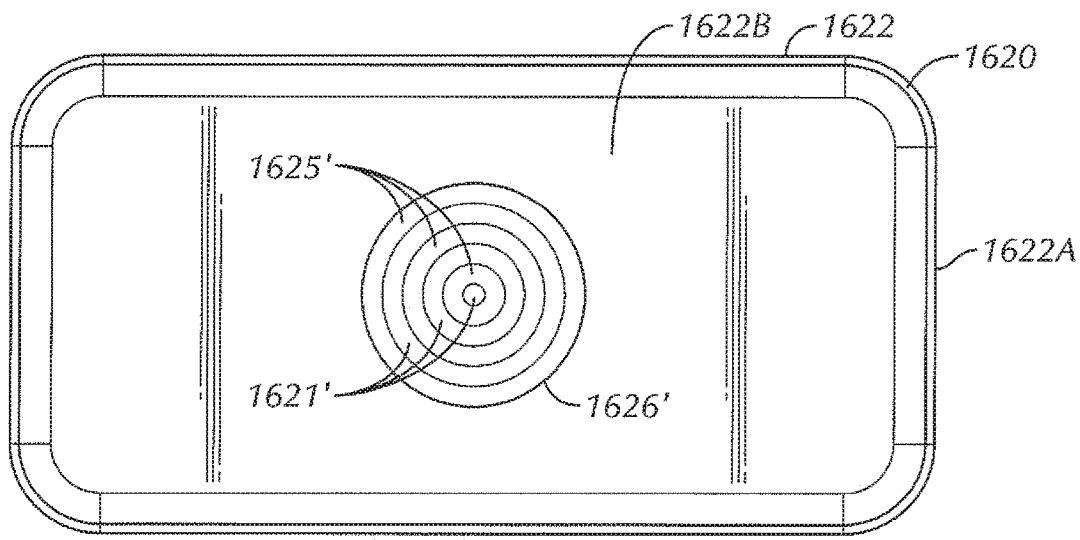
FIG. 17B is a bottom view of the sterilizable container with the alternate direct connection configuration of FIG. 17A.

In further examples, referring now to FIGS. 17A and 17B, the box 1622 of the sterilizable container can include one or more circular contacts 1621' disposed within an opening 1626' in the wall of the box 1622. Although shown disposed within the bottom 1622B of the box 1622, in other examples, it is contemplated that the opening can be in other walls of the box 1622, such as one or more of the sidewalls 1622A. In some examples, the box 1622 includes an insulation layer 1625' between the metal of the box 1622 and the one or more circular contacts 1621' in order to insulate the one or more contacts 1621' from the box 1622. In some examples, the box 1622 includes two or more contacts 1621' disposed within the opening 1626', with insulation layers 1625' disposed between the box 1622 and the contacts 1621' and between the contacts 1621' themselves. In some examples, the two or more contacts 1621' are substantially concentrically disposed with respect to one another, such that the contacts 1621' and insulation layers 1625' substantially resemble a bulls-eye pattern. In some examples, and as shown in FIGS. 17A and 17B, three contacts 1621' are shown, allowing for a positive lead, a negative lead, and a ground. In other examples, more or less than three contacts are contemplated within the box 1622. In some examples, the one or more contacts 1621' can be used in a manner similar to the contacts 1621 described above to directly transfer power from the base 1610 through the wall of the box 1622 and into the interior 1622C of the box 1622 without breaching the sterile barrier formed by the sterilizable container 1620. In some examples, the metallic box 1622 itself can be used as a contact, although that would cause the entire sterilizable container 1620 to become part of the electrical power transfer. In some examples, the one or more contacts 1621' can be used with a radio-frequency signal.

In various examples, such as with respect to the example direct connection systems 1600 described herein, instead of or in addition to powering one or more electrical devices 1680 disposed within the sterilizable container 1620, the series of contacts 1612, 1621, 1621', 1631 can be used to send communication signals to the base 1610 or other communication station and/or to the one or more electrical devices 1680. For instance, using one of the example systems 1600, an electrical device 1680 can communicate state of health (SOH), an error, state of charge (SOC), a charge level indication, a temperature indication, and/or other information or data to the base 1610 or other communication system. Alternatively or additionally, in some examples, the base 1610 or other communication system can be used to send information, data, and/or instructions to the one or more electrical devices 1680, such as a discharge command, a charge level inquiry, a temperature inquiry, and/or the like.

Figure 19:
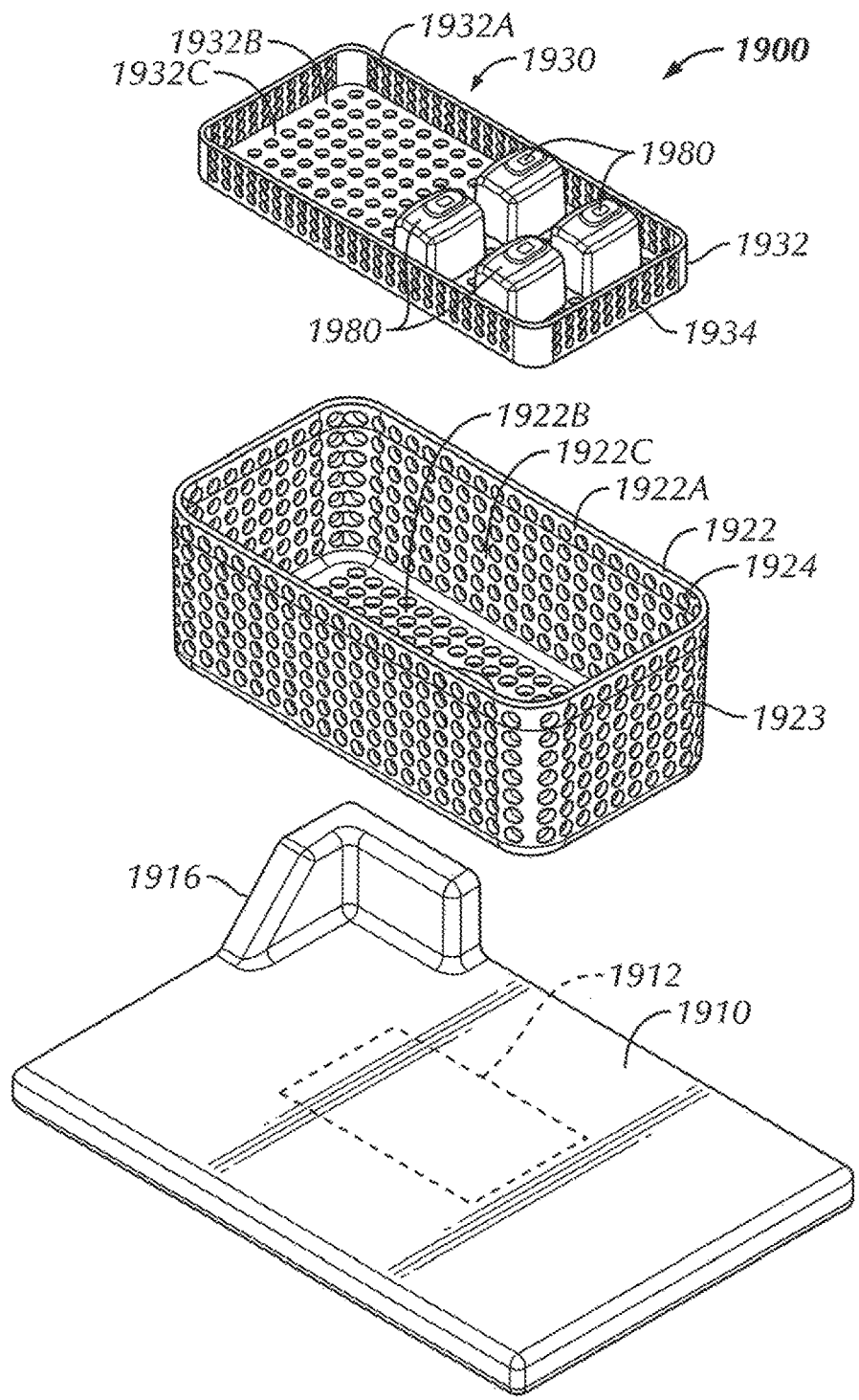
FIG. 19 is an exploded view of a system in accordance with at least one example of the invention.
Figure 20:
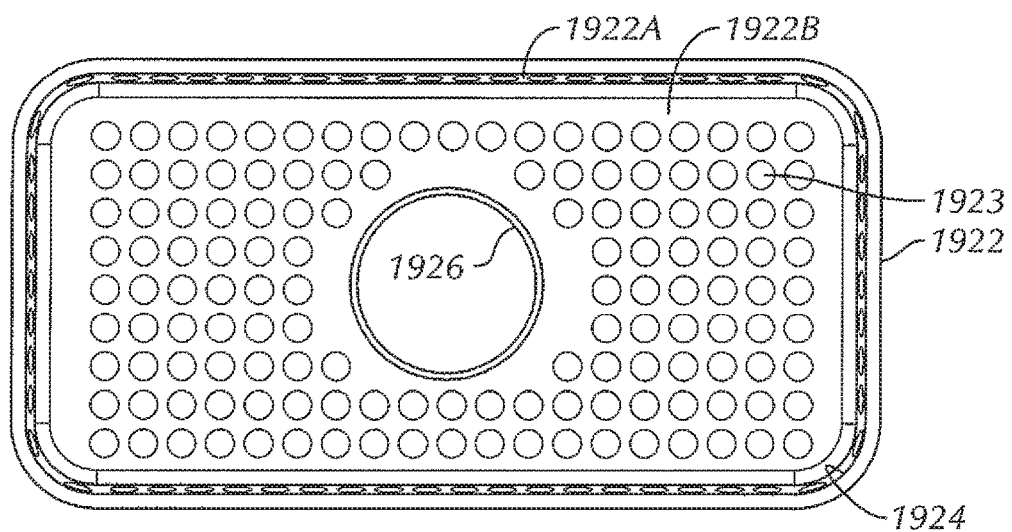
FIG. 20 is a top view of a component tray of a tray of the system of FIG. 19.

Referring to FIGS. 19 and 20, in some examples, a system 1900 is configured to wirelessly power an electrical device 1980 within a sterilizable vessel 1920. In some examples, an interior of the sterilizable vessel 1920 is sized and shaped to accommodate at least one electrical device 1980 within the interior of the sterilizable vessel 1920. In some examples, as will be described in more detail herein, a power generating device 1910 is configured to generate and transfer power to the electrical device 1980. In some examples, the sterilizable vessel 1920 is configured to accommodate the electrical device 1980, the sterilizable vessel 1920 being configured to allow power to be at least partially wirelessly transferred from the power generating device 1910, through the sterilizable vessel 1920, and to the electrical device 1980.

In some examples, the sterilizable vessel 1920 includes a sterilizable tray 1920 similar to the tray 720 (FIGS. 7-9) described herein. In various examples, the sterilizable tray 1920 can be formed from a metallic material. For instance, in some examples, the sterilizable tray 1920 can be formed from stainless steel. In other examples, the sterilizable tray 1920 can be formed from aluminum. In some examples, the sterilizable tray 1920 includes a bottom portion 1922 including sidewalls 1922A and a bottom 1922B, the bottom portion 1922 including an opening 1924 to access an interior 1922C of the box 1922. In some examples, the opening 1924 is in a top of the bottom portion 1922. The sterilizable tray 1920, in some examples, includes a closure or lid (for instance, similar to the lid 728 of FIGS. 7 and 8) that, when in a closed position, closes off the opening 1924 of the bottom portion 1922. In some examples, the bottom portion 1922 includes apertures or openings 1923 to allow steam and heat of an autoclave to penetrate the interior 1922C of the sterilizable tray 1920 to sterilize the contents, such as one or more electrical devices 1980, of the sterilizable tray 1920.

Within the interior 1922C of the sterilizable tray 1920, in some examples, is a component tray 1930 configured to hold one or more components, such as one or more electrical devices 1980, within the sterilizable tray 1920 for sterilization. In some examples, the component tray 1930 is removable from within the interior 1922C of the sterilizable tray 1920. In some examples, the component tray 1930 includes a tray portion 1932 having sidewalls 1932A and a bottom 1932B, the tray portion 1932 defining an interior 1932C configured to hold one or more components therein, for instance, during an autoclave process or other sterilization procedure. In some examples, at least a portion of the tray portion 1932 includes holes or openings 1934 therethrough to allow steam and/or heat from the autoclave process or other sterilization procedure to penetrate the interior 1932C of the tray portion 1932 and envelop the one or more components in order to sterilize the one or more components. In some examples, the component tray 1930 is sized and shaped to freely slide into and out of the interior 1922B of the bottom portion 1922, for example, when a user is inserting the component tray 1930 into the bottom portion 1922 and taking the component tray 1930 out of the bottom portion 1922, for instance, to insert or remove one or more components (such as one or more electrical devices 1980).

In some examples, an antimicrobial material or wrap (for instance, similar to the antimicrobial wrap 740 of FIG. 9) can be used to wrap the sterilizable tray 1920 prior to sterilization, wherein the antimicrobial material allows the contents, such as one or more electrical devices 1980, of the sterilizable tray 1920 to be sterilized during autoclaving and maintains the sterile barrier after sterilization.

In some examples, the system 1900 includes the power generating device 1910. In some examples, the power generating device 1910 is a base 1910 that is sized and shaped to allow a sterilizable tray 1920 to be placed on top of the base 1910. The base 1910, in some examples, is connectable to power, such as, but not limited to, by plugging a power cord of the base 1910 into a wall outlet. The base 1910 includes, in various examples, a source coil 1912 positioned within the base 1910 so as to be in proximity to the sterilizable tray 1920 with the sterilizable tray 1920 being situated on or otherwise in place with respect to the base 1910. In some examples, the source coil 1912 of the base 1910 is configured to generate an electromagnetic field for wirelessly transferring power to the one or more electric devices 1980.

Due to the enclosed nature of a typical sterilizable tray, the passing of the electromagnetic field and, in turn, the transferring of power, through a typical sterilizable tray is at least hindered, if not completely obstructed. While the sterilizable tray 1920 of the present system includes the openings 1923 within the bottom portion 1922, in some examples, the openings 1923 are not sufficient to allow for efficient power transfer through the wall of the bottom portion 1922. For this reason, in some examples, the sterilizable tray 1920 includes an aperture or opening 1926 in the bottom portion 1922. By using an aperture or opening 1926 to permit a signal to pass through the wall of the sterilizable tray 1920, power can be transmitted directly through the sterilizable tray 1920 substantially as would be expected in the absence of an enclosure.

In some examples, the base 1910 can include an alignment feature 1916 configured to assist in aligning the source coil 1912 with the opening 1926 of the sterilizable tray 1920. In some examples, the alignment feature 1916 includes a protrusion extending from a top surface of the base 1910 that corresponds to a corner of the bottom portion 1922, such that when the corner of the bottom portion 1922 is seated against the corresponding structure of the alignment feature 1916, the opening 1926 of the bottom portion 1922 of the sterilizable tray 1920 is disposed above or otherwise aligned with the source coil 1912 of the base 1910, thereby aiding in the positioning of the sterilizable tray 1920 on the base 1910 for power transfer. In other examples, various other alignment features are contemplated, including, but not limited to, one or more ribs or other features sized, shaped, or otherwise configured to allow the sterilizable tray 1920 to be seated thereon or therewithin in order to align the sterilizable tray 1920 with respect to the source coil 1912. In other examples, the alignment feature can include one or more grooves sized, shaped, or otherwise configured to allow the sterilizable tray 1920 to be seated within the one or more grooves in order to align the sterilizable tray 1920 with respect to the source coil 1912. In still other examples, the base 1910 can include one or more markings on the base 1910 to facilitate alignment of the sterilizable tray 1920 with respect to the source coil 1912.

In some examples, the opening 1926 is disposed within the bottom 1922B of the bottom portion 1922, although in other examples, the opening can be disposed within other portions of the bottom portion 1922, depending upon the positioning of the source coil 1912 within the base 1910. In some examples, the opening 1926 of the sterilizable tray 1920 is positioned to be aligned with the source coil 1912 of the base 1910 with the sterilizable tray 1920 in position for power transfer on the base 1910. In some examples, the size and shape of the opening 1926 is configured to allow for the electromagnetic waves transmitted by the source coil 1912 of the base 1910 to relatively efficiently pass through the wall (for instance, the bottom 1922B) of the bottom portion 1922 and into the interior 1922C of the bottom portion 1922. Although shown in FIG. 20 having a large circular shape, the size and shape of the opening 1926 is not limited as such, and, in various examples, includes various shapes such as rectangular, elliptical, triangular, or the like, or that there be more than one opening 1926 in the wall of the bottom portion 1922, provided the configuration allows for a sufficient amount of electromagnetic waves to pass into the interior 1922C of the bottom portion 1922.

In some examples, the electromagnetic waves transmitted by the source coil 1912 are received by a receiving coil (for instance, similar to the receiving coil 182 of the electromagnetic device 180 described above) affixed to each of the one or more electrical devices 1980. In some examples, the receiving coil is disposed within each of the one or more electrical devices 1980. In some examples, the receiving coil is tuned with respect to the source coil 1912 in order to efficiently receive electromagnetic waves from the source coil 1912.

In some examples, a proximity of the opening 1926 to the source coil 1912 or otherwise to the electromagnetic signal is a concern because of resonant matching with the receiving coil of the one or more electrical devices 1980 disposed within the sterilizable tray 1920. Shield currents, as described above, can result in detuning, which can reduce the effectiveness of the wireless power transfer between the source coil 1912 and the receiving coil of the one or more electrical devices 1980. In some examples, by placing the opening 1926 directly in between the source coil 1912 and the receiving coil of the one or more electrical devices 1980, the detuning effect from the shield currents can be minimized and power transfer can be maximized through the opening 1926. That is, in some examples, with the receiving coil of at least one of the electrical devices 1980 being directly above the opening 1926 and the source coil 1952 being directly below the opening 1926, proximity of the coils for tuning purposes can be maintained, thereby reducing potential interference of the shield current counter-field with the resonant tuning. In some examples, the proximity of the coils combined with a properly sized opening 1926 can permit the maximum amount of electromagnetic signal to pass through the wall of the sterilizable tray 1920 and deliver power to the one or more electrical devices 1980 disposed within the sterilizable tray 1920.

In this way, in some examples, with the one or more electrical devices 1980 disposed within the sterilizable tray 1920, power can be transferred from the source coil 1912 of the base 1910, through the opening 1926 of the bottom portion 122, and into the interior 1922C of the bottom portion 1922 to be received by the receiving coil of each of the one or more electrical devices 1980 in order to wirelessly power the one or more electrical devices 1980. In some examples, the one or more electrical devices 1980 include one or more batteries 1980 configured to be wirelessly charged by the base 1910. That is, in some examples, the system 1900 is configured to wirelessly charge the one or more batteries 1980 within the sterilizable tray 1920. Furthermore, in some examples, the opening 1926 of the bottom portion 1922 allows for power to be transferred through the bottom portion 1922 with little to no obstruction from the bottom portion 1922.

In some examples, with the component tray 1930 being used within the sterilizable tray 1920 during wireless powering, it is possible that the component tray 1930 can interfere with the wireless transfer of power between the base 1910 and the one or more electrical devices 1980 since a portion of the component tray 1930 (for instance, the bottom 1932B of the component tray 1930) would be disposed in between the base 1910 and the one or more electrical devices 1980. For this reason, the component tray 1930, in various examples, can be configured to limit, if not eliminate, interference and/or obstruction with the wireless transfer of power. For instance, in some examples, the component tray 1930 includes an insert (for instance, similar to the insert 136 of the component tray 130 described above) formed from a material that allows electromagnetic waves to pass through more efficiently than a metallic material. In some examples, the insert can be formed from a polymeric material. In further examples, the insert can be formed from a plastic material. In other examples, the insert can be formed from other materials that allow electromagnetic waves to pass through with little to no interference, such as, but not limited to, glass, ceramic, or the like. In some examples, it is contemplated that the entire component tray 1930 is formed from a material that allows electromagnetic waves to pass through more efficiently than a metallic material, such as, but not limited to, a polymeric material, a plastic material, glass, ceramic, or the like, or a combination thereof. In other examples, the component tray 1930 can include openings in the tray portion 1932, the openings being configured to allow for electromagnetic waves to pass therethrough. In some examples, the holes or openings 1934 can be configured to allow for efficient passage of electromagnetic waves therethrough. In further examples, the tray portion 1932 can include openings that are shaped differently from the openings 1934 shown in FIG. 19 to further enhance the efficiency of the passage of electromagnetic waves through the tray portion 1932. For instance, in some examples, one or more of the openings can include an elongated shape (rectangular or elliptical, for instance) or a larger diameter than that of the openings 1934. That is, in various embodiments, variously shaped openings of the tray portion 1932 are contemplated herein, provided the openings provide for relatively efficient transfer of power through the component tray 1930 between the source coil 1912 of the base 1910 and the receiving coil of the one or more electrical devices 1980.

The examples of the system 1900 allow for wireless power transfer from the base 1910 to the one or more electrical devices 1980 disposed within the sterilizable tray 1920 via the source coil 1912 within the base 1910 and the receiving coil within each of the one or more electrical devices 1980. That is, in some examples, the opening 1926 in the wall of the sterilizable tray 1920 is configured to allow wireless power transfer through the wall of the sterilizable tray 1920 from the base 1910 to the one or more electrical devices 1980. The sterile field within the sterilizable tray 1920 can be maintained because the sterile barrier formed by the antimicrobial wrap around the sterilizable tray 1920 is not breached, and the one or more electrical devices 1980 are able to be immersively sterilized in that the one or more electrical devices 1980 are wirelessly powered and do not require the one or more electrical devices to be plugging in, potentially obstructing at least a portion of the one or more electrical devices 1980 from being fully sterilized.

Figure 21:
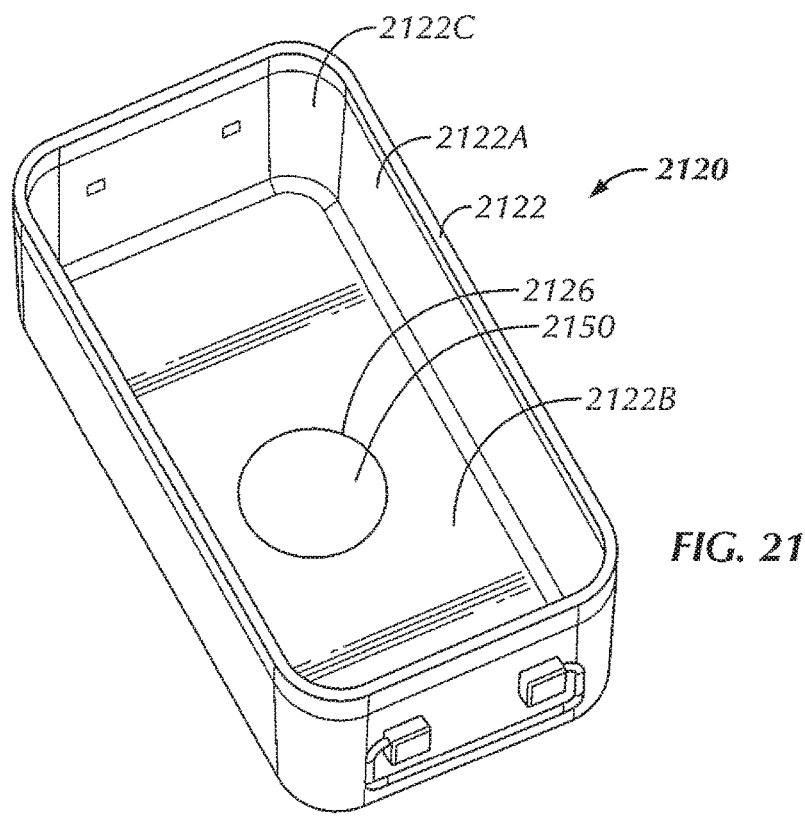
FIG. 21 is a perspective view of a sterilizable container of a system in accordance with at least one example of the invention.

Although the system 1900 of FIGS. 19 and 20 is shown with a sterilizable tray 1920, other types of sterilizable vessels can be used. For instance, referring to FIG. 21, a sterilizable container 2120 can be used, in some examples. That is, in some examples, a box 2122 of the sterilizable container 2120 can include a hole, aperture, or opening 2126 within a wall of the sterilizable container 2120. In some examples, the opening 2126 is disposed within a bottom 2122B of the box 2122. In other examples, the opening can be disposed within one or more sidewalls 2122A of the box, either instead of or in addition to being disposed within the bottom 2122B. In further examples, more than one opening can be disposed within one or more of the walls of the box 2122. However, in some examples, since sterilizable containers 2120 are not typically wrapped with an antimicrobial material or wrap, breaching of the exterior of the sterilizable container 2120 should be avoided in order to maintain the sterile barrier of the sterilizable container 2120 after it has been sterilized. For this reason, the opening 2126 of this example should not remain open like the opening 1926 of the sterilizable tray 1920 described above. As such, in some examples, an insert 2150 is disposed within the opening 2126. In further examples, the insert 2150 is sealingly engaged within the opening 2126. The insert 2150, in various examples, is affixed within the opening 2126 of the box 2122 using various methods of affixation including, but not limited to, fastening using one or more screws or other fasteners, affixation using one or more adhesives, affixation using a welding technique (laser, ultrasonic, or the like), affixation by molding of the insert 2150 directly within the opening 2126 and to the box 2122, or the like. In this way, the insert 2150 sealed within the opening 2126 of the box 2122 can maintain the sterile barrier within an interior 2122C of the sterilizable container 2120 after it has undergone a sterilization process. In some examples, the insert 2150 is formed from a non-metallic and/or non-magnetic material so as to allow electromagnetic waves to pass through the insert 2150 and the opening 2126 in order to allow wireless power transfer from a source coil disposed within a power generating device or base (for instance, the source coil 1912 of the base 1910). In further examples, the insert 2150 is formed from a material that allows electromagnetic waves to pass through more efficiently than a metallic material. In some examples, the insert 2150 can be formed from a polymeric material. In further examples, the insert 2150 can be formed from a plastic material. In other examples, the insert 2150 can be formed from other materials that allow electromagnetic waves to pass through with little to no interference, such as, but not limited to, a glass material, a ceramic material, or the like. In further examples, the insert 2150 can be formed from various materials, including, but not limited to one or more of polyether ether ketone (PEEK), polysulfone, polyetherimide (PEI), ceramic, polytetrafluoroethylene (PTFE), and/or poly methyl methacrylate (PMMA).

In some examples, rather than just forming an insert from a non-metallic material and/or non-magnetic material, it is contemplated that an entire wall of a sterilizable vessel (including a sterilizable tray, a sterilizable container, or another type of sterilizable vessel) is formed from a non-metallic and/or non-magnetic material. For instance, in some examples, the entire bottom of the sterilizable vessel can be formed from a non-metallic and/or non-magnetic material. In other examples, the entire box of a sterilizable vessel can be formed from a non-metallic and/or non-magnetic material. The eddy currents that create electromagnetic shields in metallic enclosures do not exist in other materials. For instance, plastic and/or ceramic materials lack the free electrons that can be induced to motion by the electromagnetic field, and are therefore invisible to electromagnetic fields. In some examples, having a partially or completely non-metallic sterilizable vessel can be functionally identical to not having an enclosure at all (from a wireless power transfer standpoint), and a wall thickness of the non-metallic and/or non-magnetic material sterilizable vessel can be selected for mechanical robustness while discounting, if not eliminating, concerns about skin effect or shield currents. In this way, in some examples, at least a wall of a sterilizable vessel can include a non-metallic and/or non-magnetic material to allow wireless power transfer through the wall of the sterilizable vessel from a power generating device to one or more electrical devices disposed within the sterilizable vessel. In various examples, various materials are contemplated for a non-metallic and/or non-magnetic material sterilizable vessel, including, but not limited to, various polymeric materials suitable for use in an autoclaving process, various glass materials, various ceramic materials, or a combination thereof. In further examples, various materials are contemplated, including, but not limited to one or more of PEEK, polysulfone, PEI, ceramic, PTFE, and/or PMMA. In some examples, a PEEK material is contemplated, such as, but not limited to, a 30% glass-filled PEEK material.

Figure 22:
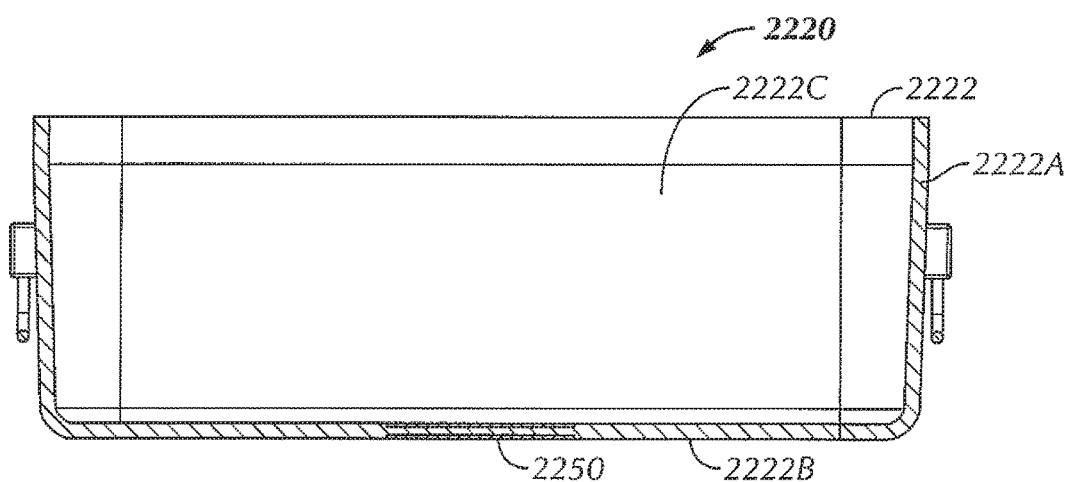
FIG. 22 is a cross-sectional view of a sterilizable container of a system in accordance with at least one example of the invention.

Referring to FIG. 22, a sterilizable container 2220, in some examples, includes a box 2222 with sidewalls 2222A and a bottom 2222B defining an interior 2222C. In some examples, the sterilizable container 2220 is formed from a metallic material, including, but not limited to stainless steel, aluminum, titanium, or the like, or a combination thereof. In various examples, various metallic materials are contemplated for use with the sterilizable container 2220, provided the metallic material is suitable for use in an autoclaving or other sterilization process. In some examples, instead of (or in addition to) having an opening like the opening 2126 of the sterilizable container 2120 described above, the box 2222 of the sterilizable container 2220 includes at least a portion 2250 having a wall thickness that is reduced from a wall thickness of the rest of the box 2222. In some examples, a thickness of the portion 2250 is configured to allow wireless power transfer through the wall of the sterilizable container 2220 from a power generating device to at least one electrical device disposed within the sterilizable container 2220. That is, at least the portion 2250 of the sterilizable container 2220 can be formed thin enough so that the skin effect of the material does not present an obstacle during energy transfer through the portion 2250. In some example, the thin-walled portion 2250 is disposed within the bottom 2222B of the box 2222. In other examples, the thin-walled portion 2250 can be disposed in other walls of the box 2222, such as one or more of the sidewalls 2222A of the box instead of, or in addition to, the bottom 2222B. In other examples, an entire side (such as, for instance, the bottom) of the box includes a reduced wall thickness. In further examples, the entire box includes a reduced wall thickness. By decreasing the thickness of at least a portion 2250 of the box, less energy from electromagnetic waves (for instance, electromagnetic waves transmitted by a coil similar to the examples of coils described herein) will be absorbed, deflected, or otherwise lost in a wireless transfer of power through the thin-walled portion 2250 compared to that energy absorbed, deflected, or otherwise lost through a portion of the box 2222 having a thicker wall. In this way, the thin-walled portion 2250 maintains the integrity of the wall of the box 2122, thereby maintaining the sterile barrier within the interior 2222C of the sterilizable container 2220 after it has undergone a sterilization process. In general, the thinner the thickness of the wall of the box 2222, the less energy that is lost when trying to wirelessly transfer power through the wall of the box 2222. However, the thinner the portion 2250 of the box 2222 is, the more likely it is that the portion 2250 can get breached or otherwise damaged through normal usage, thereby potentially breaking the sterile barrier of the sterilizable container 2220. Therefore, the present examples of the sterilizable container 2220 seek a balance between robustness of the sterilizable container 2220 and efficiency of energy transfer through the portion 2250 of the box 2222 of the sterilizable container 2220.

In some examples, either in addition to or instead of using the thin-walled portion 2250, a material can be used for the thin-walled portion 2250 of the box and/or one or more of the walls of the box 2222 that includes a relatively high resistivity metallic material. A high-resistivity material (in this example, for instance, a metallic material having a higher resistivity than stainless steel) would result in a greater skin depth of the material (greater than the skin depth of stainless steel, in this example). Because the skin depth would be larger for this high-resistivity material, electromagnetic waves can pass through a greater distance of this material, and, in turn, the thin-walled portion 2250 and/or other wall or portion of the box 2222 can include a greater thickness while still allowing electromagnetic waves to pass through. In some examples, the thickness of the portion 2250 and/or walls or other portion of the box 2222 is sufficient to withstand the rigors of sterilization and/or other use of the box 2222 while, at the same time, allowing a sufficient amount of electromagnetic waves to pass through the portion 2250 and/or walls or other portion of the box 2222 to effect wireless power transfer into the interior 2222C of the box 2222, for instance, to wirelessly power one or more electric devices disposed within the sterilizable container 2220. For instance, in some examples, various titanium materials can be used for high resistivity metallic material for the thin-walled portion 2250. In some examples, commercially pure titanium can be used for the thin-walled portion 2250. In other examples, a titanium alloy can be used for the thin-walled portion 2250. In further examples, the titanium alloy can include Titanium Grade 5, Titanium Grade 9, or another titanium alloy with resistive properties that are favorable for the thin-walled portion 2250.

In some examples, in addition to or instead of one or both of the thin-walled portion 2250 and/or the high-resistivity material, a lower frequency can be employed in the wireless power transfer to increase skin depth of the material used for the box 2222 (such as, for instance, the portion 2250 and/or other wall or portion of the box 2222). In some examples, reduced frequencies can reduce shield effectiveness, thereby lowering absorption and reflection losses. That is, in some examples, a power generating device can be configured to transmit power at a relatively low frequency (for instance, 250 kHz) that allows wireless power transfer through the wall of the sterilizable container to wirelessly transfer power from the power generating device to one or more electrical devices disposed within the sterilizable container, as is described herein. In some examples, a combination of a high-resistivity material and a low frequency can allow for wireless energy transfer to within the sterilizable container with sufficient energy left over to power a circuit within the sterilizable container (for instance, to charge or otherwise power one or more electrical devices within the sterilizable container), while maintaining a robust wall thickness of the sterilizable container that is suitable for the rigors of sterilization and/or other use of the sterilizable container.

Figure 23:
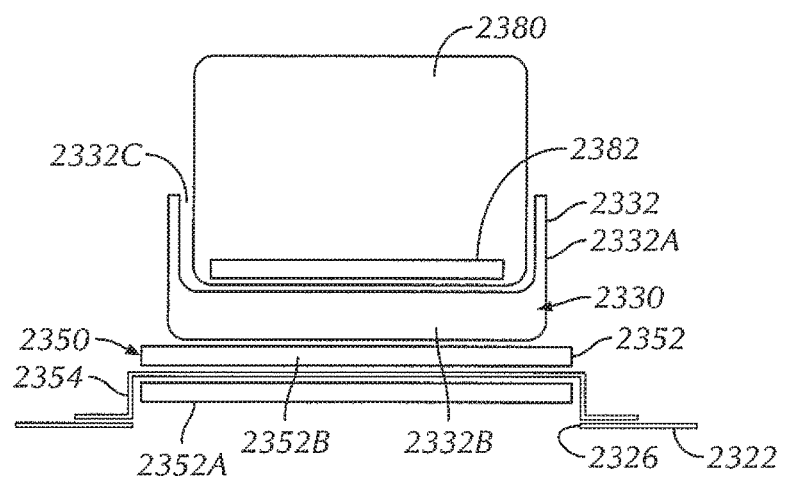
FIG. 23 is a cross-sectional view of a portion of a sterilizable vessel in accordance with at least one example of the invention, the sterilizable vessel including a formed nest.
Figures 24, 25:
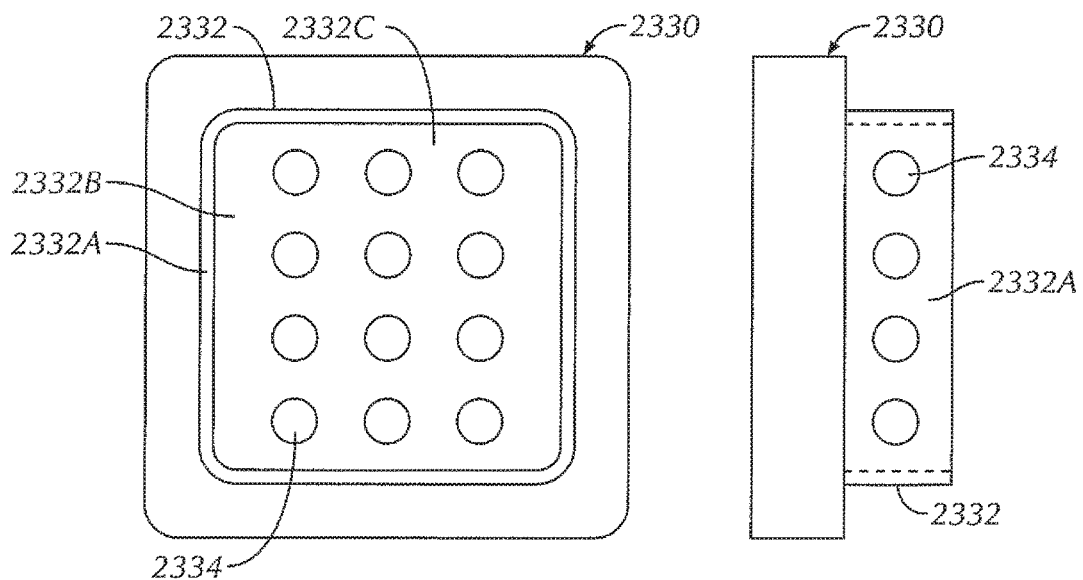
FIG. 24 is top view of the formed nest of FIG. 23.
FIG. 25 is side view of the formed nest of FIG. 23.

Referring to FIGS. 23-25, in some examples, a portion of a sterilizable vessel includes a cutout, hole, or opening 2326 in a wall of the box 2322 of the sterilizable vessel. In various examples, the sterilizable vessel can include a sterilizable container (for instance, similar to the example sterilizable containers described herein), a sterilizable tray (for instance, similar to the example sterilizable trays described herein), or other sterilizable vessel. In some examples, the opening 2326 can be similar to the openings 126, 1026, 2126 described above. In some examples, the opening 2326 is disposed within a bottom of the box 2322 of the sterilizable vessel. In other examples, the opening can be disposed within one or more other walls instead of, or in addition to, the bottom of the box 2322.

In some examples, a coil assembly 2350 is disposed within the opening 2326. The coil assembly 2350, in some examples, includes a coil 2352 disposed on an insert 2354. In some examples, the insert 2354 is affixed to the wall of the box 2322 in various ways, including, but not limited to riveting, bolting, and/or welding. In some examples, the coil 2352 includes a split-winding repeater 2352, including an external coil 2352A and an internal coil 2352B disposed on opposite sides of the insert 2354 and directly electrically coupled to one another via a conductor, via, or other electrical connection extending through the insert 2354 between the external coil 2352A and the internal coil 2352B. In some examples, the direct electrical connection between the external coil 2352A and the internal coil 2352B is sealed within the insert 2354 in order to maintain the integrity of the sterile barrier formed by the exterior of the sterilizable vessel. In some examples, the split-winding repeater 2352 can be similar to one or more of the examples of split-winding repeaters that are described in U.S. Patent Application Publication No. 2015/0207337, entitled "Split Winding Repeater," which is incorporated by reference herein in its entirety. Although shown with a split-winding repeater 2352, in other examples, other coils and/or inserts can be used, such as, but not limited to, various coils 152, 152', 1052 and/or various inserts or portions 154, 154', 1054, 2150, 2250 described herein.

In some examples, the coil assembly 2350 is configured to wirelessly power an electrical device 2380. The electrical device 2380, in some examples, includes a receiving coil 2382 configured to receive electromagnetic waves generated by the coil 2352, for instance, to wirelessly power the electrical device 2380. In some examples, the electrical device 2380 includes a battery 2380 configured to be wirelessly charged through wireless energy transfer from the coil 2352 to the receiving coil 2382.

In some examples, the insert 2354 is indented toward an interior of the box 2322 to accommodate the external coil 2352A so that the external coil 2352A does not extend out from a wall of the box 2322. In this way, an outside surface of the sterilizable vessel is substantially uniform and free of protrusions that could, for instance, make stacking the sterilizable vessel with other sterilizable vessels problematic. Furthermore, a protrusion on an outer surface of the sterilizable vessel could potentially interfere with an autoclave, inhibiting the sterilizable vessel from being sterilized in the same autoclave as standard sterilizable vessels.

In some examples, a nest 2330 is disposed within the sterilizable vessel. In some examples, the nest 2330 is shaped and sized to hold the electrical device 2380 therein. In further examples, the nest 2330 is contoured such that the electrical device 2380 fits in a particular orientation within the nest 2330. In some examples, the nest 2330 includes a holding portion 2332 including sidewalls 2332A and a bottom 2332B defining an interior 2332C of the holding portion 2332. In some examples, the sidewalls 2332A and the bottom 2332B are configured to allow the electrical device 2380 to specifically fit within the interior 2332C of the nest 2330 to maintain the electrical device 2380 in proper alignment with and proximity to the coil 2352 to facilitate efficient wireless power transfer to the electrical device 2380 from the coil 2352. In some examples, the nest 2330 is formed from a plastic material or another material that is substantially invisible to a wireless field. In further examples, the nest 2330 is formed from a high-temperature plastic material to withstand the sterilization process. In further examples, the nest 2330 includes ventilation holes 2334 within the nest 2330 to facilitate sterilization of the electrical device 2380 within the nest 2330. In some examples, the ventilation holes 2334 are disposed within at least one of the sidewalls 2332A and the bottom 2332B. In further examples, the ventilation holes 2334 are disposed within more than one of the sidewalls 2332A and the bottom 2332B. In still further examples, the ventilation holes 2334 are disposed within each of the sidewalls 2332A and the bottom 2332B. In this way, the one or more electrical devices 2380 can be held in place within the nest 2330, with the ventilation holes 2334 permitting steam to access all sides of the one or more electrical devices 2380 during sterilization, as well as allowing moisture to drain or evaporate from around and/or on the one or more electrical devices 2380. In this way, the surfaces of the one or more electrical devices 2380 are not isolated from the washing function of the autoclave.

In this way, the nest 2330 is configured to hold one or more electrical devices 2380 within the sterilizable vessel in such a way that the one or more electrical devices 2380 are maintained within the wireless field without compromising sterilizability. The one or more electrical devices 2380, in some examples, can be powered wirelessly in the same sterilizable vessel that the one or more electrical devices 2380 are sterilized in without compromising the sterile field of the sterilized vessel. The nest 2330, in some examples, allows the one or more electrical devices 2380 to be held in a repeatable location, permitting the wireless charging field to be tuned for a narrower physical range. Because the one or more electrical devices 2380 can be maintained in a repeatable location within the wireless field, the achievement of maximum wireless power transfer efficiency is facilitated.

In various examples, the opening 2326 can be formed to any size or shape, for instance, to accommodate variously sized coils and/or sterilizable vessels. In other examples, the opening 2326 can be located in any surface of the sterilizable vessel. In this way, the sterilizable vessel for wireless power transfer can be configured to be used with existing equipment, such as, but not limited to, existing autoclaves. In further examples, a standard sterilizable vessel can be retrofitted to be capable of wireless power transfer by cutting the opening 2326 into a wall of the sterilizable vessel, affixing the coil assembly 2350 within the opening 2326, and including the nest 2330.

The present inventors have recognized various advantages of the subject matter described herein. For instance, in some examples, the examples of systems, apparatuses, and methods described herein can be used to power and/or charge a device after autoclaving without breaking the sterile field. In some examples, the subject matter described herein can be used with respect to charging of a device within a sterilizable vessel. In various examples, the apparatus, system, and method can include at least an aspect of wirelessly powering and/or charging for the device within the sterilizable vessel. The present inventors have recognized the present subject matter can be used to maintain ease-of-use, allow for post-autoclave charging of batteries, and retain vessel durability. While various advantages of the example apparatuses are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. A system for wirelessly charging a battery, the system comprising:
   a power generating device configured to generate and transfer power to the battery, the power generating device electrically coupled to a source coil;
   a sterilizable vessel configured to accommodate the battery within the vessel, the vessel including an opening to allow access to an interior of the vessel, the battery including a receiving coil disposed within the battery; and
   a nest disposed within the vessel, the nest shaped and sized to hold the battery within the nest, wherein the source coil electrically coupled to the power generating device is configured to transmit electromagnetic waves to the receiving coil of the battery to wirelessly transfer power from the power generating device to the battery.

2. The system of claim 1, wherein the nest includes a holding portion including sidewalls and a bottom defining an interior of the holding portion, the interior being configured to maintain the battery in a charging position within the nest.

3. The system of claim 2, wherein, with the battery in the charging position, the nest maintains the receiving coil of the battery in an optimal changing orientation within the vessel.

4. The system of claim 2, wherein at least one of the sidewalls or the bottom of the nest includes a ventilation hole to facilitate sterilization of the battery within the nest.

5. The system of claim 4, wherein each of the sidewalls and the bottom of the nest includes at least one ventilation hole.

6. The system of claim 1, wherein the vessel includes an aperture in a wall of the vessel, the aperture being configured to allow wireless power transfer through the wall of the vessel from the power generating device to the battery within the vessel.

7. The system of claim 6, wherein an insert is disposed within the aperture of the vessel.

8. The system of claim 7, wherein the insert includes the source coil, the source coil being selectively electrically coupled to the power generating device.

9. The system of claim 7, wherein the insert includes a repeater coil configured to receive the electromagnetic waves transmitted by the source coil and transmit the electromagnetic waves to the receiving coil of the battery to wirelessly transfer power from the power generating device, through the vessel, and to the battery.

10. The system of claim 9, wherein the repeater coil includes a split-winding repeater including an external coil and an internal coil disposed on opposite sides of the insert and directly electrically coupled to one another.

11. The system of claim 10, wherein the insert is indented toward the interior of the vessel to accommodate the external coil so that the external coil does not extend out from a bottom of the vessel.

12. The system of claim 1, wherein the source coil is disposed within the power generating device.

13. A system for wirelessly recharging a battery, the system comprising:
   a power generating device configured to generate and transfer power to the battery, the power generating device being electrically coupled to a source coil;
   a sterilizable container sized and shaped to accommodate the battery within an interior of the sterilizable container, the sterilizable container including an opening to allow access to the interior of the sterilizable container and a closure, which, when in a closed position, closes the opening of the sterilizable container to seal the interior of the sterilizable container, the battery including a receiving coil disposed within the battery; and
   a nest disposed within the sterilizable container, the nest shaped and sized to hold the battery within the nest, wherein the sterilizable container is configured to allow power to be at least partially wirelessly transferred from the source coil electrically coupled to the power generating device, through the sterilizable container, and to the battery, wherein the source coil is configured to transmit electromagnetic waves to the receiving coil to wirelessly transfer power from the power generating device to the battery to charge the battery within the sealed sterilizable container.

14. The system of claim 13, wherein the nest includes a holding portion including sidewalls and a bottom defining an interior of the holding portion, the interior being configured to maintain the battery in a charging position within the nest.

15. The system of claim 14, wherein, with the battery in the charging position, the nest maintains the receiving coil of the battery in an optimal changing orientation within the vessel.

16. The system of claim 14, wherein at least one of the sidewalls or the bottom of the nest includes a ventilation hole to facilitate sterilization of the battery within the nest.

17. The system of claim 13, wherein the sterilizable container includes an aperture in a wall of the sterilizable container, the aperture being configured to allow wireless power transfer through the wall of the sterilizable container from the power generating device to the battery within the sterilizable container.

18. The system of claim 17, wherein an insert is disposed within the aperture of the sterilizable container.

19. The system of claim 18, wherein the insert includes a repeater coil configured to receive the electromagnetic waves transmitted by the source coil and transmit the electromagnetic waves to the receiving coil of the battery to wirelessly transfer power from the power generating device, through the sterilizable container, and to the battery.

20. The system of claim 19, wherein the repeater coil includes a split-winding repeater including an external coil and an internal coil disposed on opposite sides of the insert and directly electrically coupled to one another.

* * * * *